United States Patent
Hoffer et al.

(10) Patent No.: US 10,512,772 B2
(45) Date of Patent: Dec. 24, 2019

(54) TRANSVASCULAR NERVE STIMULATION APPARATUS AND METHODS

(71) Applicant: SIMON FRASER UNIVERSITY, Burnaby (CA)

(72) Inventors: Joaquin Andres Hoffer, Anmore (CA); Marc-Andre Nolette, Burnaby (CA); Viral Thakkar, Surrey (CA); Bao Dung Tran, Vancouver (CA)

(73) Assignee: Lungpacer Medical Inc., Burnaby (CA)

( * ) Notice: Subject to any disclaimer, the term of this patent is extended or adjusted under 35 U.S.C. 154(b) by 1133 days.

(21) Appl. No.: 14/383,285

(22) PCT Filed: Mar. 4, 2013

(86) PCT No.: PCT/CA2013/050159
§ 371 (c)(1),
(2) Date: Sep. 5, 2014

(87) PCT Pub. No.: WO2013/131187
PCT Pub. Date: Sep. 12, 2013

(65) Prior Publication Data
US 2015/0045810 A1 Feb. 12, 2015

Related U.S. Application Data

(60) Provisional application No. 61/606,899, filed on Mar. 5, 2012.

(51) Int. Cl.
*A61N 1/05* (2006.01)
*A61N 1/36* (2006.01)

(52) U.S. Cl.
CPC ......... *A61N 1/0551* (2013.01); *A61N 1/3601* (2013.01)

(58) Field of Classification Search
CPC . A61N 1/372; A61N 1/05; A61N 1/36; A61N 1/0551; A61N 5/145; A61N 2/86; A61F 2/86
(Continued)

(56) References Cited

U.S. PATENT DOCUMENTS

| | | |
|---|---|---|
| 1,693,734 A | 12/1928 | Waggoner |
| 2,532,788 A | 12/1950 | Sarnoff |

(Continued)

FOREIGN PATENT DOCUMENTS

| | | |
|---|---|---|
| CN | 1652839 A | 8/2005 |
| CN | 102143781 A | 8/2011 |

(Continued)

OTHER PUBLICATIONS

Pavlovic, D. et al, "Diaphragm pacing during prolonged mechanical ventilation of the lungs could prevent from respiratory muscle fatigue", Medical Hypotheses, 2003, vol. 60, No. 3, pp. 398-403.

(Continued)

*Primary Examiner* — Catherine M Voorhees
*Assistant Examiner* — Roland Dinga
(74) *Attorney, Agent, or Firm* — Bookoff McAndrews, PLLC

(57) ABSTRACT

The invention, in one aspect, relates to an intravascular electrode system. The system comprises one or more electrodes supported on an elongated resiliently flexible support member, and the support member may be used to introduce the electrodes into a blood vessel. As the support member is introduced into the blood vessel the support member bends to follow the path of the blood vessel.

38 Claims, 43 Drawing Sheets

(58) Field of Classification Search
USPC .......... 607/42, 116, 62, 2; 600/364; 606/129
See application file for complete search history.

(56) References Cited

U.S. PATENT DOCUMENTS

| | | | |
|---|---|---|---|
| 2,664,880 A | 1/1954 | Wales, Jr. |
| 3,348,548 A | 10/1967 | Chardack |
| 3,470,876 A | 10/1969 | John |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |

(56) References Cited

U.S. PATENT DOCUMENTS

| | | |
|---|---|---|
| 6,643,552 B2 | 11/2003 | Edell et al. |
| 6,651,652 B1 | 11/2003 | Ward |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venrooij et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | Ben-David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |

(56) References Cited

U.S. PATENT DOCUMENTS

| | | |
|---|---|---|
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | McCabe et al. |
| 9,168,377 B2 | 10/2015 | Hoffer |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,396 B2 | 5/2018 | Young et al. |
| 9,968,785 B2 | 5/2018 | Hoffer et al. |
| 9,968,786 B2 | 5/2018 | Bauer et al. |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |

(56) References Cited

U.S. PATENT DOCUMENTS

| | | |
|---|---|---|
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2009/0318993 A1* | 12/2009 | Eidenschink .. A61B 17/320725 607/10 |
| 2010/0022950 A1 | 1/2010 | Anderson et al. |
| 2010/0036451 A1* | 2/2010 | Hoffer ................. A61N 1/0558 607/42 |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1* | 5/2010 | Kornet ............... A61N 1/36114 607/62 |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1* | 9/2011 | Ohtaka ................ A61N 1/0551 607/122 |
| 2011/0270358 A1 | 11/2011 | Davis et al. |
| 2011/0288609 A1 | 11/2011 | Tehrani et al. |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | de la Rama et al. |
| 2015/0374991 A1 | 12/2015 | Morris et al. |
| 2016/0001072 A1 | 1/2016 | Gelfand et al. |

(56) References Cited

U.S. PATENT DOCUMENTS

| | | | |
|---|---|---|---|
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |

FOREIGN PATENT DOCUMENTS

| | | | |
|---|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | 08-510677 A | 11/1996 |
| JP | 2003-503119 A | 1/2003 |
| JP | 2010516353 A | 5/2010 |
| JP | 2011-200571 A1 | 10/2011 |
| JP | 2012/000195 A | 1/2012 |
| JP | 2012-000195 A | 1/2012 |
| WO | 9407564 A2 | 4/1994 |
| WO | WO 95/08357 A1 | 3/1995 |
| WO | 9964105 A1 | 12/1999 |
| WO | 9965561 A1 | 12/1999 |
| WO | 0100273 A1 | 1/2001 |
| WO | 02058785 A1 | 8/2002 |
| WO | WO 03094855 | 11/2003 |
| WO | 2006110338 A1 | 10/2006 |
| WO | 2006115877 A1 | 11/2006 |
| WO | 2007053508 A1 | 5/2007 |
| WO | 2008092246 A1 | 8/2008 |
| WO | 2008094344 A1 | 8/2008 |
| WO | 2009006337 A1 | 1/2009 |
| WO | 2009134459 A2 | 11/2009 |
| WO | WO 2010/029842 A1 | 3/2010 |
| WO | WO 2011/158410 | 6/2010 |
| WO | 2010148412 A1 | 12/2010 |
| WO | 2012106533 A2 | 8/2012 |
| WO | 2013131187 A1 | 9/2013 |
| WO | 2013188965 A1 | 12/2013 |

OTHER PUBLICATIONS

Search Report—Patent Office of the People's Republic of China, dated Jul. 24, 2015, in corresponding Application No. CN 2013/80023357.5.
Search Report—European Patent Office, dated Nov. 12, 2015, in corresponding Application No. EP 13758363.
Levine, et al., New England Journal of Medicine, 358: 1327-1335, 2008.
De Gregorio, M.A. et al., "The Gunther Tulip Retrievable Filter: Prolonged Temporary Filtration by Repositioning within the Inferior Vena Cava", J Vasc Interv Radiol, 14:1259-1265, 2003.
Onders, R. et al., "Diaphragm pacing with natural orifice transluminal endoscopic surgery: potential for difficult-to-wean intensive care unit patients", Surg Endosc, 21:475-479, 2007.
Sarnoff, S.J. et al., "Electrophrenic Respiration", Science, 108:482, 1948.
Marcy, T.W. et al., "Diaphragm Pacing for Ventilatory Insufficiency", Journal of Intensive Care Medicine, vol. 2, No. 6, pp. 345-353, 1987.
Hoffer, J.A. et al., Diaphragm Pacing with Endovascular Electrodes, Sep. 2010.
Daggett, W.M. et al., "Intracaval electrophrenic stimulation. I. Experimental Application During Barbiturate Intoxication Hemorrhage and Gang", Journal of Thoracic and Cardiovascular Surgery,51(5):676-884, 1966.
Furman, S., "Transvenous Stimulation of the Phrenic Nerves", Journal of Thoracic and Cardiovascular Surgery, 62 (5):743-751, 1971.
Wanner, A. et al., "Trasvenous phrenic nerve stimulation in anesthetized dogs", Journal of Applied Physiology, 34 (4):489-494, 1973.
Daggett, W.M. et al., "Intracaval electrophrenic stimulation. II. Studies on Pulmonary Mechanics Surface Tension Urine Flow and Bilateral Ph", Journal of Thoracic and Cardiovascular Surgery, 60(1):98-107, 1970.
Japanese Office Action in corresponding Japanese Application No. 2014-560202, dated Dec. 6, 2016 (4 pages).
European Search Report dated Sep. 8, 2017 in corresponding European Patent Application No. 17169051.4 (7pages).
Japanese Office Action dated Oct. 17, 2017 in corresponding Japanese Patent Application No. 2014-560202 (5 pages).
Escher, Doris J.W. et al., "Clinical Control of Respiration by Transvenous Phrenic Pacing," American Society for Artificial Internal Organs: Apr. 1968—vol. 14—Issue 1—pp. 192-197.
Ishii, K. et al., "Effects of Bilateral Transvenous Diaphragm Pacing on Hemodynamic Function in Patients after Cardiac Operations," J. Thorac. Cardiovasc. Surg., 1990.
Antonica A., et al., "Vagal Control of Lymphocyte Release from Rat Thymus," Journal of the Autonomic Nervous System, Elsevier, vol. 48(3), Aug. 1994, pp. 187-197.
Ryas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.
Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.
Borovikovaa L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.
Borovikovaa L.V., et al., "Vagus Nerve Stimulation Attenuates the Systemic Inflammatory Response to Endotoxin," Nature, Macmillan Magazines Ltd, vol. 405, May 25, 2000, pp. 458-462.
Co-pending U.S. Appl. No. 15/606,867, filed May 26, 2017.
Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.

(56) References Cited

OTHER PUBLICATIONS

Frisch S., "A Feasibility Study of a Novel Minimally Invasive Approach for Diaphragm Pacing," Master of Science Thesis, Simon Fraser University, 2009, p. 148.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Kawashima K., et al., "Extraneuronal Cholinergic System in Lymphocytes," Pharmacology & Therapeutics, Elsevier, vol. 86, 2000, pp. 29-48.
Lungpacer: Therapy, News . . . Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.
Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. S715-S728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of IκBα in Mediation of Immunosuppression by Glucocorticoids," Science, vol. 270, Oct. 13, 1995, pp. 283-286.
Sher, M.E, et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors?," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al., "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.
Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.
Whaley K, et al., "C2 Synthesis by Human Monocytes is Modulated by a Nicotinic Cholinergic Receptor," Nature, vol. 293, Oct. 15, 1981, pp. 580-582 (and reference page).

\* cited by examiner

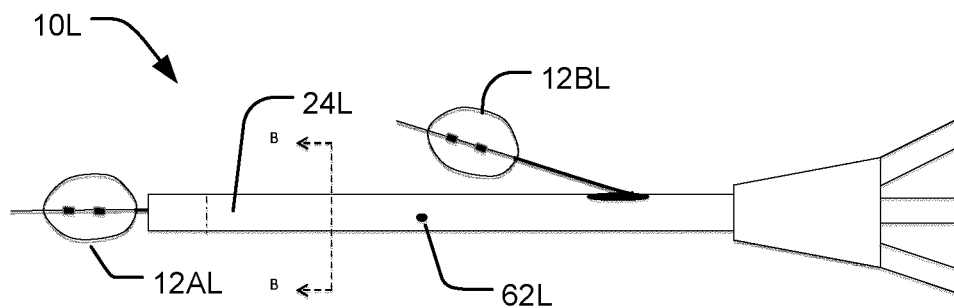
FIGURE 14A
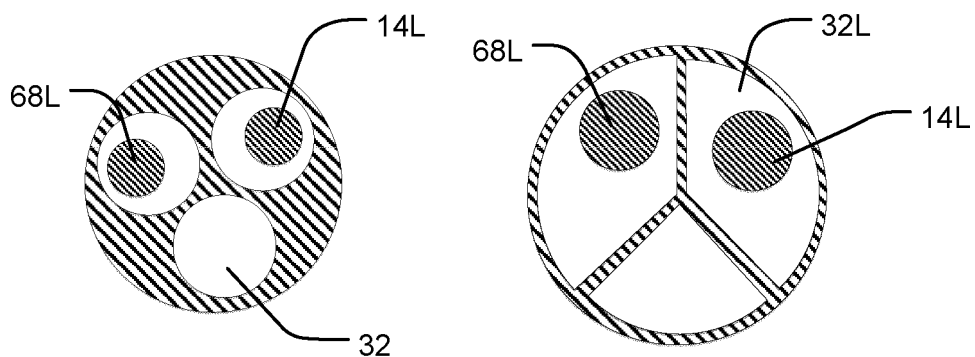
FIGURE 14B
FIGURE 14C

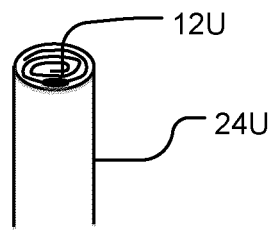
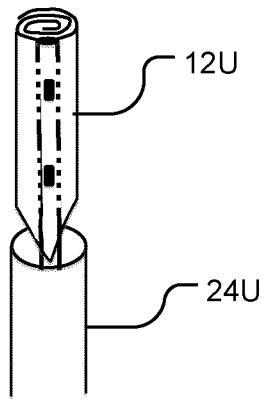
FIGURE 24A  FIGURE 24B
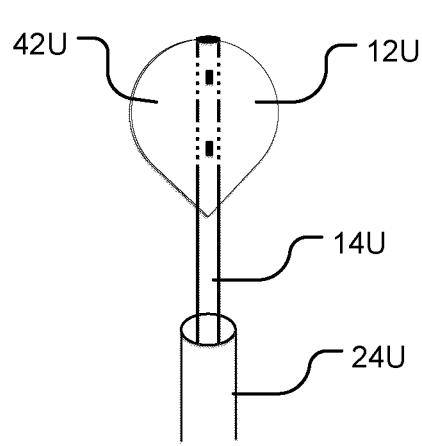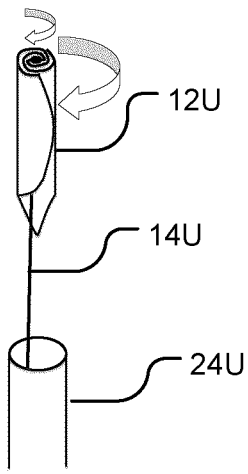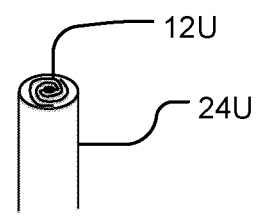
FIGURE 24C  FIGURE 24D  FIGURE 24E

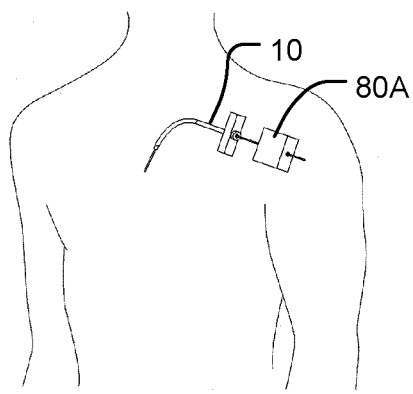
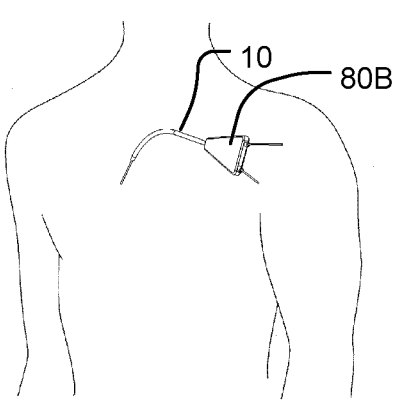
FIGURE 29A
FIGURE 29B
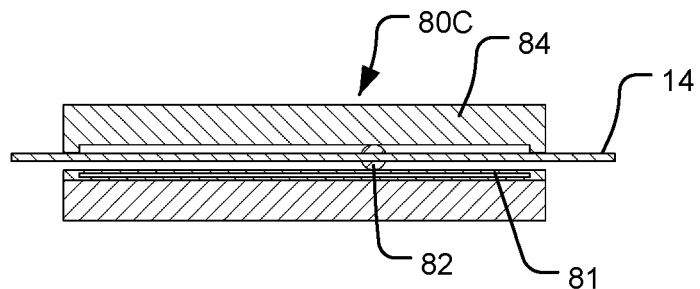
FIGURE 29C
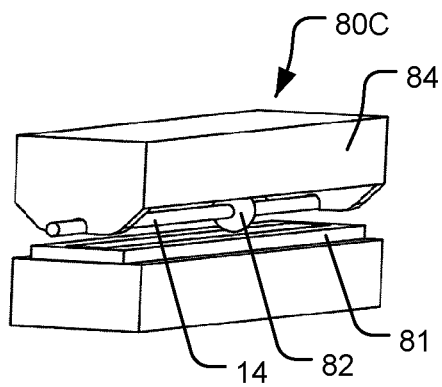
FIGURE 29D
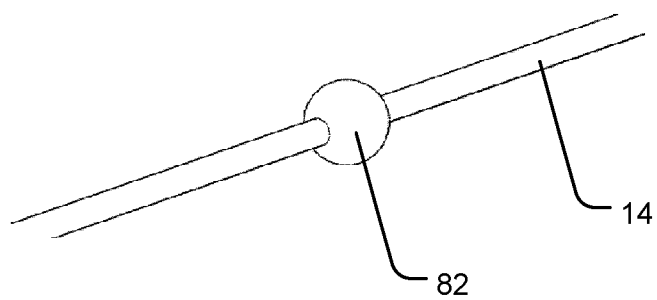
FIGURE 29E

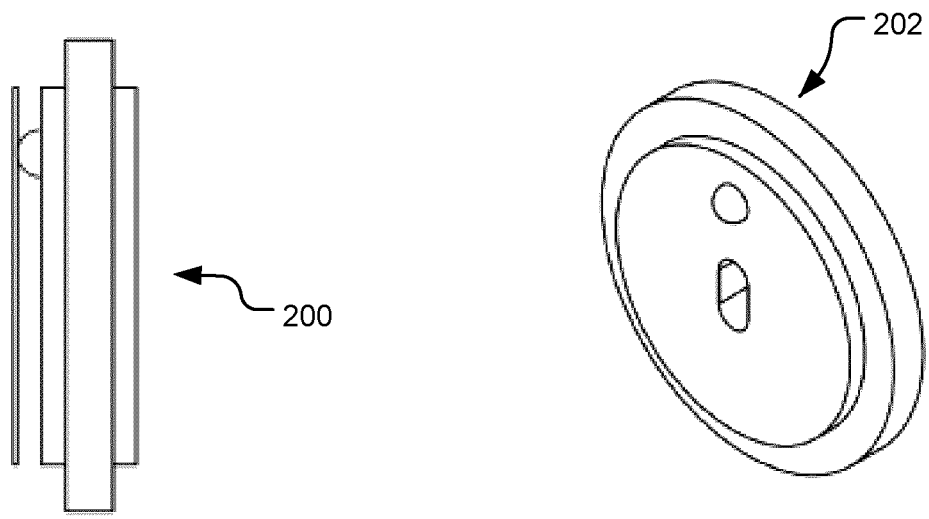
FIGURE 30A
FIGURE 30B
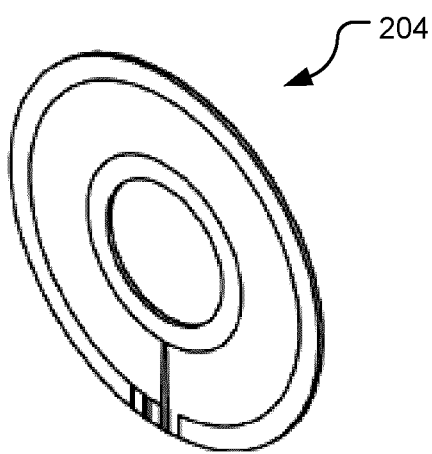
FIGURE 30C

TRANSVASCULAR NERVE STIMULATION APPARATUS AND METHODS

CROSS REFERENCE TO RELATED APPLICATIONS

This application claims priority from U.S. Application No. 61/606,899 filed 5 Mar. 2012. For purposes of the United States, this application claims the benefit under 35 U.S.C. § 119 of U.S. Application No. 61/606,899 filed 5 Mar. 2012 and entitled TRANSVASCULAR NERVE STIMULATION APPARATUS AND METHODS which is hereby incorporated herein by reference for all purposes.

TECHNICAL FIELD

The invention relates to neurophysiology and in particular to apparatus and methods for stimulating nerves through the walls of blood vessels. Non-limiting embodiments include nerve stimulation apparatus, electrode structures, electrodes and related methods.

BACKGROUND

Nerve stimulation can be applied in the treatment of a range of conditions. Nerve stimulation may be applied to control muscle activity or to generate sensory signals. Nerves may be stimulated by surgically implanting electrodes in or near the nerves and driving the electrodes from an implanted or external source of electricity.

The phrenic nerves normally carry signals that cause the contractions of the diaphragm that are necessary for breathing. Various conditions can prevent appropriate signals from being delivered to the phrenic nerves. These include:
  chronic or acute injury to the spinal cord or brain stem;
  Amyotrophic Lateral Sclerosis (ALS);
  disease affecting the spinal cord or brain stem; and,
  decreased day or night ventilatory drive (e.g. central sleep apnea, Ondine's curse).
These conditions affect a significant number of people.

Mechanical ventilation (MV) may be used to help patients breathe. Some patients require chronic mechanical ventilation and many more patients require temporary mechanical ventilation. Mechanical ventilation can be lifesaving but has a range of significant problems and/or side effects. Mechanical ventilation:
  tends to provide insufficient venting of the lungs. This can lead to accumulation of fluid in the lungs and susceptibility to infection and pneumonia.
  requires apparatus that is not readily portable.
  can adversely affect venous return because the lungs are positively pressurized.
  interferes with eating and speaking.
  requires costly maintenance and disposables.
  tends to cause positive pressure ventilator induced lung injury (VILI) and ventilator associated pneumonia (VAP).

A patient on mechanical ventilation is tied to a ventilator, and does not breathe independently. This can lead to atrophy of the diaphragm muscle (ventilator induced diaphragmatic dysfunction; VIDD) and an overall decline in well being. Muscle atrophy can occur surprisingly rapidly and can be a serious problem. In patients on mechanical ventilation, the central respiratory drive of the diaphragm is suppressed. The inactivity of the diaphragm muscle causes rapid disuse atrophy. According to a published study (Levine et al., *New England Journal of Medicine*, 358: 1327-1335, 2008), the diaphragm muscle could shrink by 52-57% after just 18-69 hours of mechanical ventilation and sedation. Ventilator-induced diaphragm atrophy could cause a patient to become ventilator-dependent. Patients in intensive care units (ICU) who become dependent on mechanical ventilation (MV) are at high risk of complications such as ventilator-acquired pneumonia (VAP) and nosocomial infections and are seven times more likely to die in the ICU. It has been reported that in 2008, 1.58 million ICU patients in the United States require MV every year, of which 20-30% (about 400,000 mechanically ventilated patients) have difficulty weaning from MV and are at risk of becoming ventilator-dependent.

Three methods have been used to reverse or slow down atrophy in disused diaphragm muscles by stimulating the phrenic nerves and are discussed below.

Method 1. Phrenic nerve pacing uses electrodes implanted in the chest to directly stimulate the phrenic nerves. The Mark IV Breathing Pacemaker System available from Avery Biomedical Devices, Inc. of Commack, N.Y., USA, is a diaphragmatic or phrenic nerve stimulator that has surgically implanted receivers and electrodes mated to an external transmitter by antennas worn over the implanted receivers. Implanting electrodes and other implantable components for phrenic nerve pacing requires significant surgery. The surgery is risky and complicated by the fact that phrenic nerves are thin (approximately 2 mm in diameter) and delicate. The surgery involves significant cost.

Method 2. Laproscopic diaphragm pacing developed by biomedical engineers and physician researchers at Case Western Reserve University is another technique for controlling breathing. Laproscopic diaphragm pacing involves placing electrodes at motor points of the diaphragm.

Method 3. A method using intravascularly implanted electrodes to stimulate a nerve has been developed by Joaquin Andres Hoffer and is described in U.S. patent application Ser. No. 12/524,571 (published on Feb. 11, 2010 as US2010/00336451) entitled "Transvascular Nerve Stimulation Apparatus And Methods", which is hereby incorporated by reference.

Method 3 has advantages over Methods 1 and 2, because it does not require invasive surgery that would typically be performed under full anaesthesia. Furthermore, ICU patients are not typically eligible for Methods 1 and 2.

There remains a need for cost-effective, practical, surgically simple and minimally invasive apparatus and methods for nerve stimulation. There is also a need for apparatus and methods for facilitating patients on MV to breathe more naturally and to be weaned from MV. There is also a need for cost effective, practical apparatus and methods for installing and/or removing nerve stimulation apparatus.

SUMMARY OF THE INVENTION

This invention has a number of aspects. Aspects of the invention include: designs for intravascular electrodes; electrode structures; nerve stimulation apparatus; intravascular apparatus including electrodes and structures for introducing and supporting the electrodes; catheters equipped with electrodes; methods for nerve stimulation; and methods for measuring the location of an electrode structure within a blood vessel relative to a target nerve. While these and other aspects may be applied together, individual aspects may be applied separately as well as in other combinations and contexts. For example, electrode structures as described herein may be applied in combination with various deployment systems known in the art for various diagnostic and/or therapeutic applications.

Aspects of the invention may be applied for restoring breathing, treating conditions such as muscle atrophy, chronic pain, and other uses involving nerve stimulation. Aspects of the invention may be applied in the treatment of acute or chronic conditions. Aspects of the invention may be applied to conveniently deploy and remove electrode structures in a patient.

One aspect of the invention relates to transvascular stimulation of nerves. In transvascular stimulation, suitable arrangements of one or more electrodes are positioned in a blood vessel that passes close to a nerve to be stimulated. Electrical currents pass from the electrodes through a wall of the blood vessel to stimulate the target nerve.

One aspect of the invention relates to transvascular stimulation of nerves in the neck and chest of a human or other mammals (e.g., a pig). FIG. 1A illustrates the anatomy of selected nerves and blood vessels in the neck and chest of a human and, in particular, the relative locations of the left and right phrenic nerves (PhN), vagus nerves (VN), internal jugular veins (IJV), brachiocephalic veins (BCV), superior vena cava (SVC) and left subclavian vein (LSV).

Further aspects of the invention and features of example embodiments are illustrated in the appended drawings and/or described in the text of this specification and/or described in the accompanying claims.

BRIEF DESCRIPTION OF THE DRAWINGS

The accompanying drawings illustrate non-limiting example embodiments of the invention.

FIG. 14A shows another embodiment of a nerve stimulation apparatus. FIGS. 14B and 14C show some possible cross sections of a tubular member of the apparatus of FIG. 14A.

FIG. 18A is a top plan view of the electrode structure. FIG. 18B is a bottom perspective view of the electrode structure.

FIGS. 24A-24E show how an example electrode structure may be rolled up, deployed, and retracted into a tubular member.

DETAILED DESCRIPTION

Figure 1A:
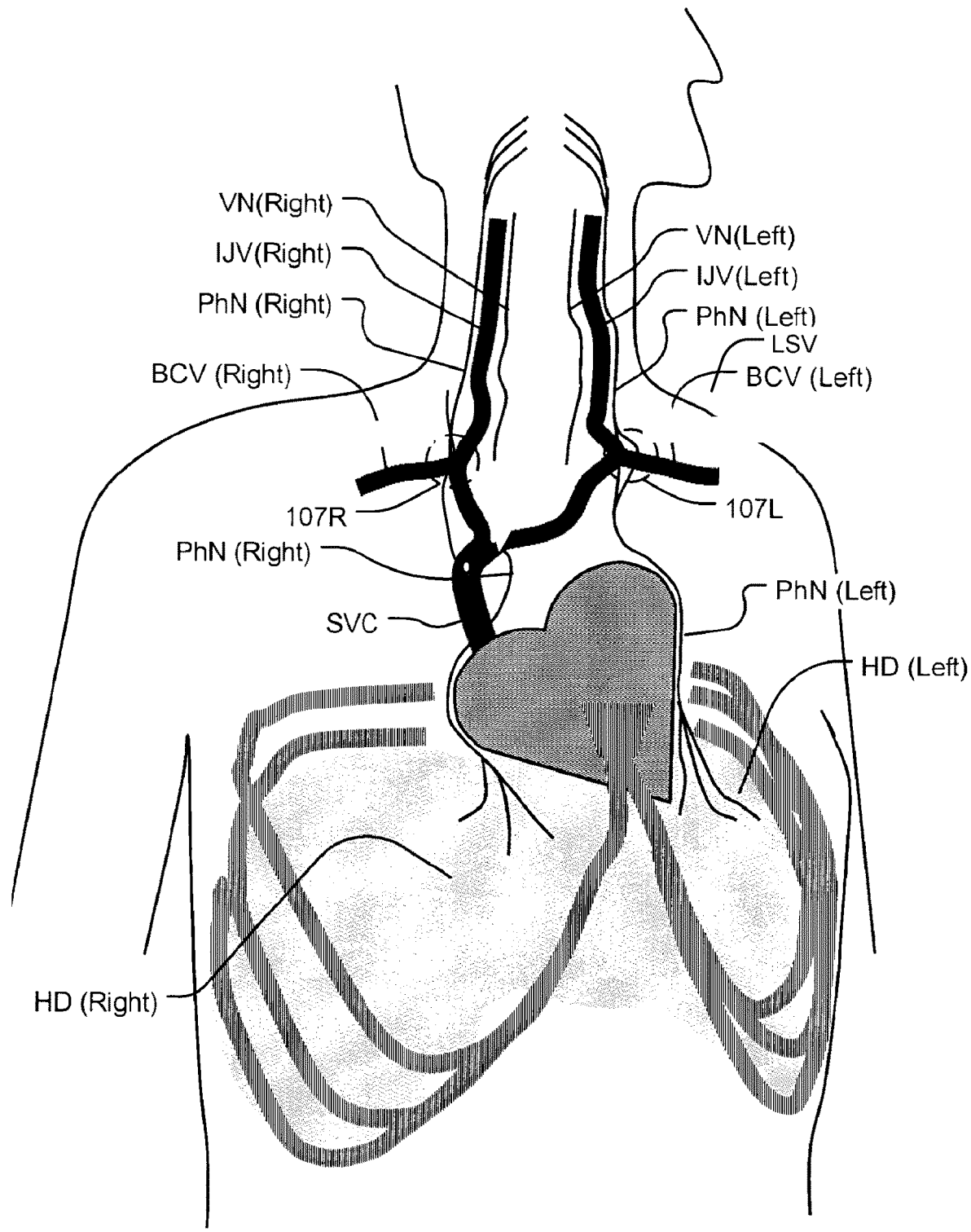
FIG. 1A illustrates the anatomy of selected nerves and blood vessels in a person's neck and upper torso.

Throughout the following description, specific details are set forth in order to provide a more thorough understanding of the invention. However, the invention may be practiced without these particulars. In other instances, well-known elements have not been shown or described in detail to avoid unnecessarily obscuring the invention. Accordingly, the specification and drawings are to be regarded in an illustrative, rather than restrictive.

Apparatus according to some embodiments provides intravascular electrode systems which include one or more electrodes supported on an elongated resiliently flexible support member. The support member may be used to introduce the electrodes into a blood vessel. As the support member is introduced into the blood vessel the support member bends to follow the path of the blood vessel. Restoring forces resulting from the resilience of the support member hold the one or more electrodes in place against the wall of the blood vessel. The electrode structure may comprise flexible electrically insulating pads that insulate electrodes from being in direct contact with blood in the main passage of the blood vessel.

In some embodiments the apparatus includes two or more electrodes at spaced-apart locations along the support member. Spacing between the electrodes may be selected to allow the electrodes to be located proximate to anatomical structures, for example nerves passing nearby the blood vessel. In an example embodiment, electrodes are spaced apart on a support structure and oriented so that an intravascular electrode system may be placed with electrodes located to stimulate a patient's left and right phrenic nerves. The electrodes may optionally have different circumferential orientations with respect to a longitudinal centerline of the support structure.

In some embodiments the support member is more flexible in one direction than in another. This can help to preserve a desired orientation of electrodes while the electrode system is being introduced into a blood vessel.

In some embodiments the electrode system comprises a catheter having one or more lumens. The catheter may provide the functionality of a central catheter of the type commonly used in intensive care units, for example. Such embodiments provide the advantage of electrodes that may be applied, for example, for stimulating nerves (e.g. for diaphragm pacing) and/or for monitoring electrical activity in the body of a patient in the same package as a central catheter that may be required in any event. In some embodiments, the catheter also serves as a support structure as described above.

Some embodiments comprise electrode structures comprising electrodes and asymmetrical electrically-insulating backing sheets. The backing sheets can electrically isolate the electrodes from blood in the lumen of a blood vessel, thereby allowing more efficient stimulation of extravascular structures such as nearby nerves. The asymmetrical arrangement of the backing sheet allows the backing sheet to be rolled into a compact configuration for insertion of the electrode structure into a blood vessel while providing a backing sheet that can provide electrical insulation for two or more electrodes. In some embodiments the backing sheet has a generally trapezoidal configuration. The backing sheet may be formed so that it tends to unroll from the rolled configuration. The backing sheet may be formed with a natural curvature similar to that of a wall of a blood vessel against which the backing sheet will be deployed. The backing sheet may be but need not be completely electrically insulating. Such a backing sheet can be advantageous as long as it provides a resistance to the flow of electricity substantially greater than the resistance that would be provided by blood in the blood vessel in the absence of the backing sheet. Such electrode structures may be applied in a wide range of intravascular applications.

Some embodiments provide electrode structures that include a retainer that holds a backing sheet in place. The retainer may comprise, for example, a formed piece of wire that extends through apertures in the backing sheet. In some embodiments the retainer comprises a pair of wire sections, which may be generally parallel, that are each woven through apertures in the backing sheet. Distal ends of the wire sections may be joined. The wire sections may be parts of a continuous wire. Distal ends of the wire sections may be bent back over the backing sheet. In some embodiments the retainer is electrically conductive and may be applied as one electrode, for example a reference electrode for electrical measurements and/or one of two or more electrodes for delivery of stimulation. The backing sheet may be rolled around the retainer for introduction into a blood vessel. Such electrode structures may be applied in a wide range of applications.

Some embodiments provide electrode structures in which a backing sheet for one or more electrodes is provided by a wall of an inflatable structure. The structure may be inflated to hold the electrodes against a wall of a blood vessel. The structure may, for example, be located on a side of a catheter or other support member. In some embodiments, inflation of the inflatable structure actuates a backing member carrying one or more electrodes to move toward engagement with a wall of a blood vessel.

Some embodiments provide intravascular electrode structures on which one or more electrodes is supported on a support member which include integrated position-measurement transducers for measuring a displacement of an electrode along a blood vessel into which the electrode is being inserted. The apparatus, including the position-measurement transducers may be intended to be disposable after a single use. Various embodiments of example position measurement transducers that can provide accurate position measurement in a suitable form factor and/or may be fabricated inexpensively are described below.

The following description describes examples of nerve stimulation apparatus and components suitable for application in nerve stimulation. In some cases the examples given are adapted for stimulation of phrenic nerves in a human or other mammals. The nerve stimulation apparatus described herein has a number of features which are particularly advantageous in combination with one another but can also be used individually, in other combinations, or in combination with the features described in US2010/00336451.

Figure 2A:
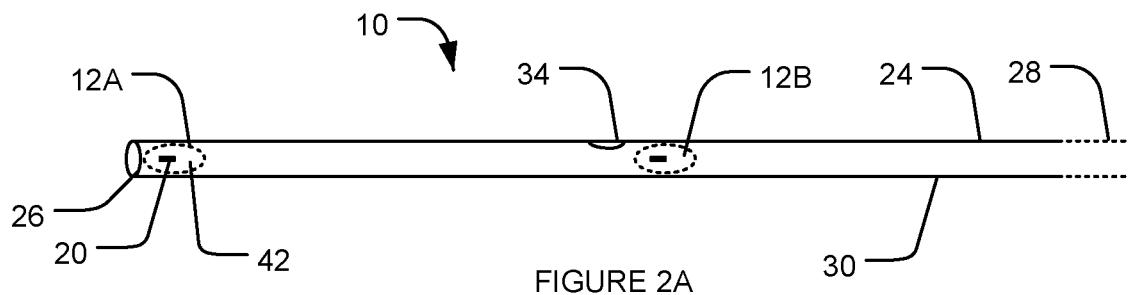
FIGS. 2A-2D are schematic views of a nerve stimulation apparatus according to an example embodiment of the invention.
Figure 2B:
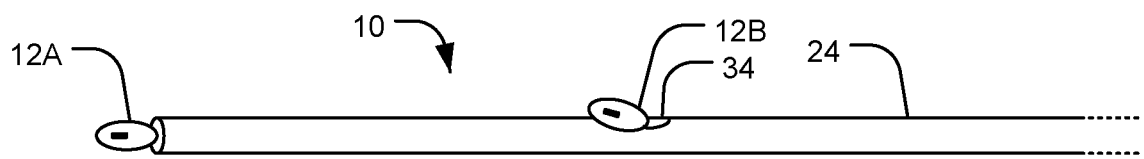
Figure 2C:
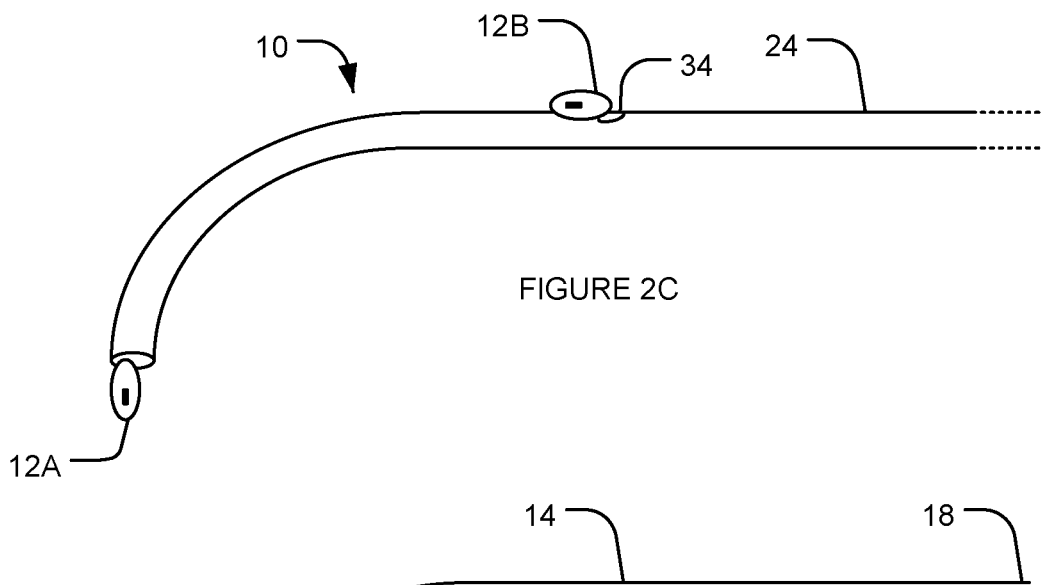

FIGS. 2A-2C are schematics of a nerve stimulation apparatus 10 according to an example embodiment of the invention. Nerve stimulation apparatus 10 comprises electrode structures 12A, 12B (collectively 12). Nerve stimulation apparatus 10 also comprises a tubular member 24. Tubular member 24 may be a catheter or cannula-type tubular member. For example, tubular member 24 may be a central venous catheter. Tubular member 24 is capable of being inserted into a lumen of a blood vessel.

Tubular member 24 has a distal end 26, a proximal end 28, an outer wall or sheath 30 that extends from distal end 26 to proximal end 28. Tubular member 24 may comprise one or more internal lumens (not specifically indicated in FIGS. 2A-2C—examples of such lumens are shown in other Figs.) For example, tubular member 24 may be a multi-lumen catheter.

In the example embodiment, at least one lumen extends longitudinally from proximal end 28 to distal end 26. The lumens may have exit openings on wall 30 of tubular member 24. These openings may be spaced apart along the length of tubular member 24. The lumens may be used for removing blood samples, inserting medication, delivering fluids or nutrients, measuring chemical or physical parameters in blood, such as pH or temperature, and the like. For example, agents may be applied through one or more of the openings to prevent clot formation on electrode structures 12. In FIG. 2A, an example opening 34 is shown, which provides an exit port for electrode structure 12B. Opening 34 may be upstream from electrode structure 12B relative to a direction of blood flow in a blood vessel in which nerve stimulation apparatus 10 is deployed.

Tubular member 24 may be flexible. A range of materials may be used for construction of tubular member 24, including silicone, polyurethane, or other suitable polymers, stainless steel, and the like. Tubular member 24 may have markings for length determination. In some embodiments, tubular member 24 is more flexible in one bending direction than in another bending direction. In some embodiments, different sections of tubular member 24 have different levels of flexibility. For example, the distal part of tubular member 24 may be more flexible than the proximal part of tubular member 24.

Electrode structure 12A is positioned at or near distal end 26 of tubular member 24. Electrode structure 12B is positioned at a mid-portion of tubular member 24. Electrode structures 12A, 12B are movable between a retracted position (i.e., received in tubular member 24) and a deployed position (i.e., extending out of tubular member 24). When electrode structures 12A, 12B are in a retracted position, electrode structures 12A, 12B are located inside or mostly inside tubular member 24 (FIG. 2A). When electrode structure 12A, 12B are in a deployed position, electrode structure 12A extends out of a distal opening of tubular member 24, and electrode structure 12B extends out of tubular member 24 from an opening 34 on wall 30 (FIGS. 2B and 2C). Typically, electrode structure 12 is dimensioned so that, when in a deployed position inside a blood vessel, it will extend approximately 45° to 60° of the way around a wall of the blood vessel, although this is not mandatory.

In FIGS. 2A-2C, a representative electrode 20 is shown for each electrode structure 12. However, it should be noted that each electrode structure 12 may comprise a plurality of electrodes. For example, one or more electrodes may be used for stimulating a target nerve; and one or more additional electrodes may be used for ECG monitoring. In some embodiments, one electrode may function as a cathode and another electrode may function as an anode. Electrode structure 20 also comprises an insulating pad 42.

Figure 2D:
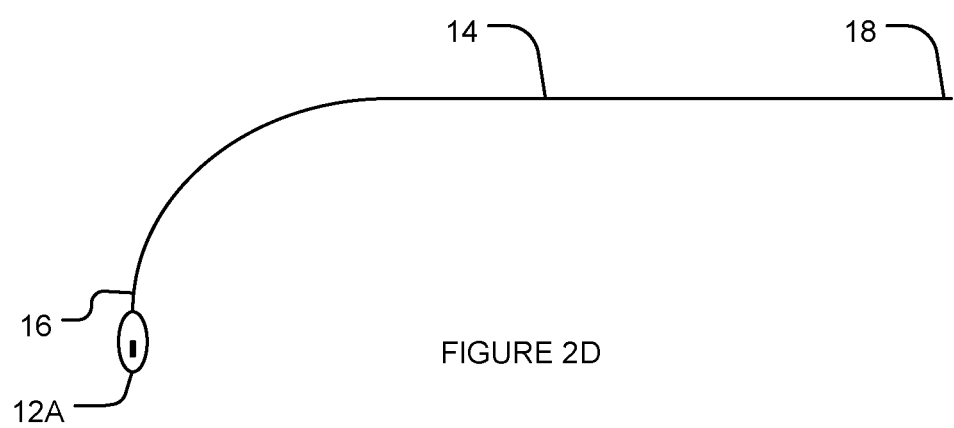

Each electrode structure 12 may be coupled to an elongated flexible shaft portion 14 which extends inside tubular member 24. Shaft portion 14 is not directly visible in FIGS. 2A-2C, but FIG. 2D schematically shows a shaft portion 14 coupled to electrode 12A, without tubular member 24. In FIG. 2D, elongated flexible shaft portion 14 has a distal end 16 and a proximal end 18. Electrode structure 12A is coupled to distal end 16 of shaft portion 14. Shaft portion 14 may comprise, for example, a single wire or tube or a plurality of wires or tubes. Shaft portion 14 may comprise one or more suitable leads (not specifically indicated in FIG. 2D, as leads may be hidden inside shaft portion 14) which may electrically couple one or more electrodes 20 to an apparatus for monitoring electrical activity and/or delivering electrical stimulation by way of electrodes 20. The leads and the electrodes 20 may be electrically coupled in a one-to-one relationship such that each electrode 20 is individually addressable. In some embodiments, some groups of two or more electrodes 20 are connected to a common lead. The leads may be carried in or along shaft portion 14.

At equilibrium, shaft portion 14 may have a configuration that is straight or curved. Shaft portion 14 may have an initial radius of curvature greater than a radius of curvature of the left brachiocephalic vein (BCV) and superior vena cava (SVC) into which nerve stimulation apparatus 10 may be introduced. Shaft portion 14 may be resilient and tending to return to its original configuration; thus, distal end 16 of shaft portion 14 tends to spring toward the far wall of the superior vena cava (SVC) when nerve stimulation apparatus 10 is inserted in a patient from the left side of the body (e.g., from LSV into BCV and SVC). This is convenient because the right phrenic nerve typically runs alongside the far wall of the superior vena cava (SVC) at this point.

In some embodiments, shaft portion 14 is more flexible in one direction than in another direction. For example, shaft portion 14 may be oriented such that it is easier to bend downwardly than sideways. This facilitates insertion and positioning of shaft portion 14 in SVC which extends downwardly from the BCV.

In some embodiments, different parts of shaft portion 14 have different levels of flexibility. For example, the distal part of shaft portion 14 may be more flexible than the proximal part of shaft portion 14. In some embodiments, flexibility of the shaft portion may vary along the length of the shaft portion. Shaft portion 14 may be made of stainless steel or other suitable material (e.g., Nitinol, high-density plastics, elastomers etc.). In some embodiments shaft portion 14 comprises a pair of flexible stainless steel tubes that are attached together by, for example, welding.

Figure 3A:
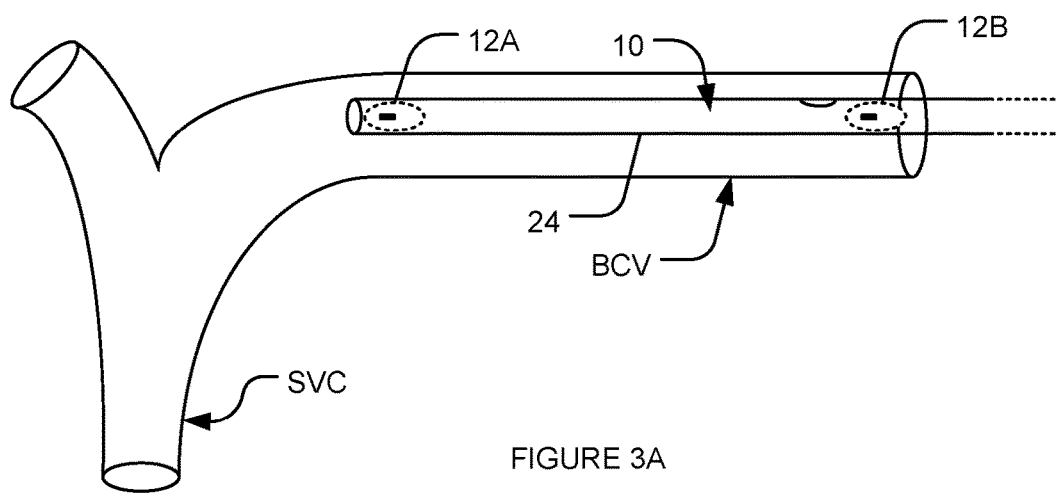
FIGS. 3A-3C illustrate the operation of nerve stimulation apparatus.
Figure 3B:
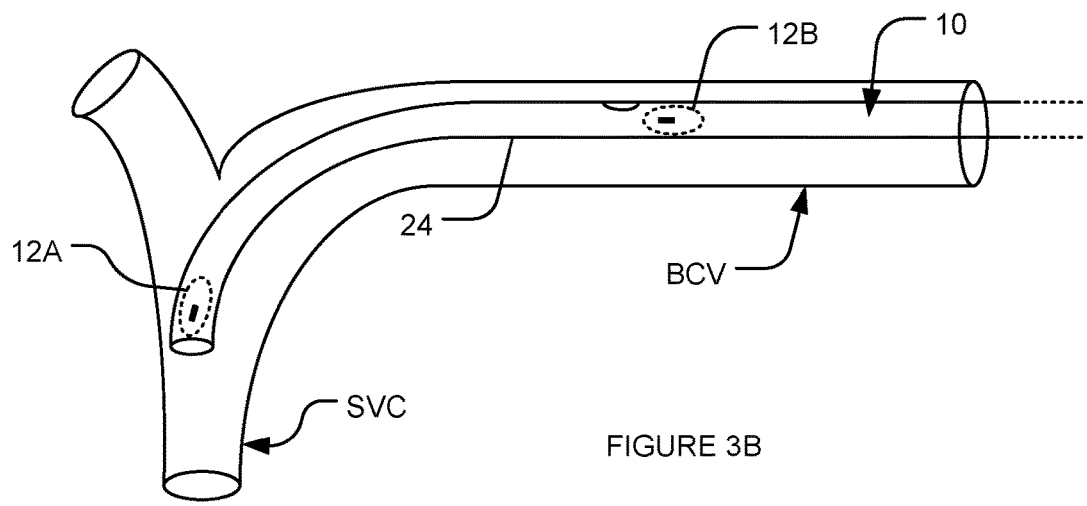
Figure 3C:
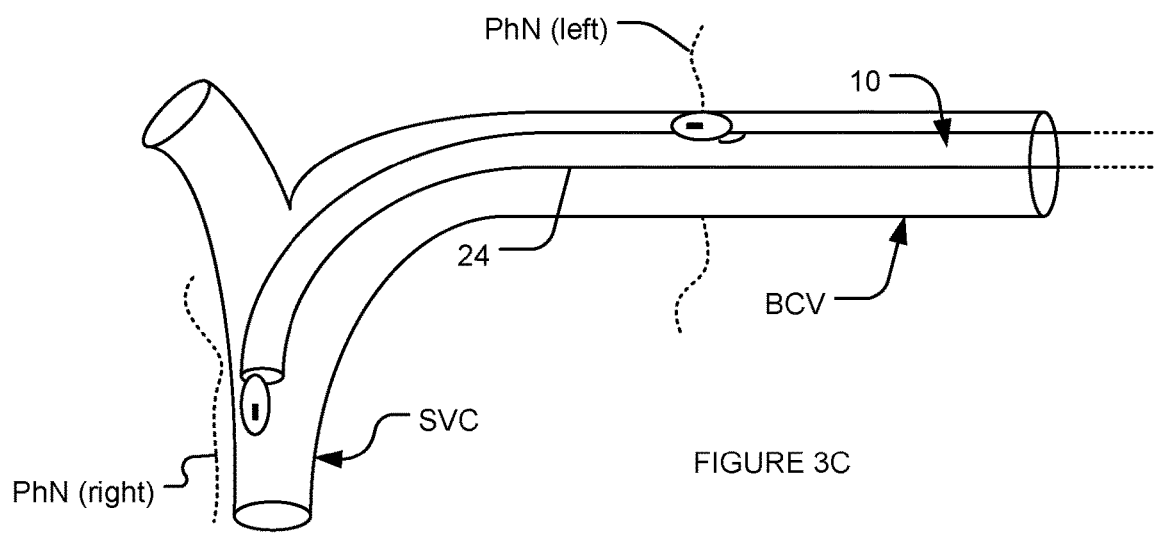

The operation of nerve stimulation apparatus 10 is schematically shown in FIGS. 3A-3C. Nerve stimulation apparatus 10 may be inserted into a person's subclavian vein and SVC as follows. The electrode structures 12A, 12B are initially located within tubular member 24. A percutaneous puncture is made into the patient's LSV. Tubular member 24 is then inserted through the puncture into the LSV. Such insertion could be done under local anaesthesia. General anaesthesia is typically not required. Tubular member 24 of nerve stimulation apparatus 10 is then advanced into the patient's left BCV and eventually into SVC. Care should be taken not to advance tubular member 24 into the right atrium of the heart. When the distal portion of tubular member 24 reaches the SVC, the distal portion of tubular member 24 bends downwardly. Electrode structures 12A, 12B are moved from a retracted position (FIG. 3B) to a deployed position (FIG. 3C). Electrode structures 12A, 12B are positioned adjacent the left and right phrenic nerves. As described below, monitoring may be performed during insertion to locate the electrode positions which allow for most effective stimulation of the phrenic nerve.

In the deployed position, electrode structures 12A, 12B extend out of tubular member 24. Electrodes 20 are pressed against a wall of the blood vessel, whereas the insulating pads 42 of the electrode structures 12A, 12B prevent the electrodes 20 from being in close electrical contact with the bulk of the blood flowing through the blood vessel. The curvature of nerve stimulation apparatus 10 may conform to the curvature of the patient's left BCV and SVC. The two electrode structures 12A, 12B may be arranged roughly at 90° to one another about the longitudinal axis of nerve stimulation apparatus 10, with electrode structure 12A oriented toward the right phrenic nerve and electrode structure 12B oriented toward the left phrenic nerve.

Testing may be done to locate electrode structures 12A, 12B at desired positions relative to the left and right phrenic nerve. Methods for locating an electrode structure relative to a target nerve are described below herein (see FIGS. 28A, 28B). Measurements can also be made to determine which electrode or electrodes of an electrode structure comprising multiple electrodes most effectively stimulate the target nerve.

Once nerve stimulation apparatus 10 has been properly inserted into a patient as described above, electrodes 20 are electrically coupled to a stimulation device (e.g., a pulse generator which may be optionally located outside the body) to apply electric current to the phrenic nerves, causing the diaphragm muscle to contract. The contraction of the diaphragm muscle causes inhalation of air into the lungs. When the electric stimulation of the phrenic nerves is stopped, the diaphragm muscle relaxes and exhalation occurs. This allows the patient to breathe more naturally. Nerve stimulation apparatus 10 may be used in combination with a control unit (e.g., a bedside control unit).

Nerve stimulation apparatus 10 may be removed from the patient's body. During removal, electrode structures 12A, 12B may be first moved from a deployed configuration (FIG. 3C) to a retracted configuration (FIG. 3B). Once the electrode structures 12A, 12B are retrieved into tubular member 24, the entire nerve stimulation apparatus 10 may be withdrawn from the patient's body. Alternatively, removing may not require retraction of electrode structure into the tubular member. Preferred methods for retrieving nerve stimulation apparatus 10 from the patient's body have a number of advantages which include one or more of: (1) nerve stimulation apparatus 10 can be repositioned easily for replacement or if the electrode moves with respect to target nerves, for example while the patient is being moved or transferred; (2) periodic removal of nerve stimulation apparatus prevents the build-up of plaques, or inflammation, or other undesirable physiological or pathological consequences as a result of implanting nerve stimulation apparatus in a blood vessel; (3) nerve stimulation apparatus 10 can be conveniently removed from the patient when nerve stimulation treatment is no longer needed.

Figure 4A:
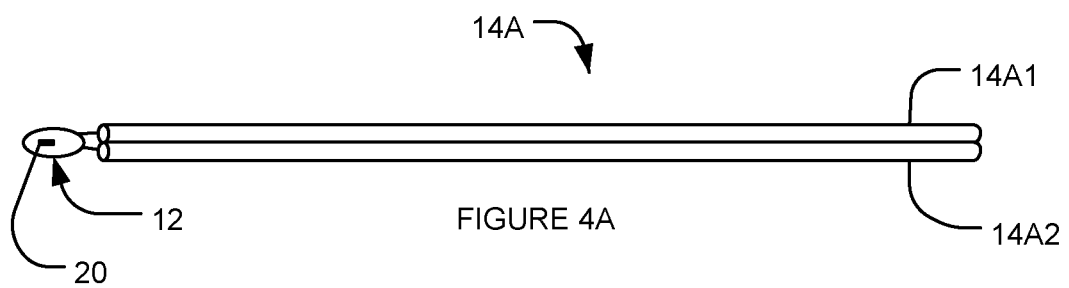
FIG. 4A illustrates a shaft portion comprising a pair of attached tubes.

Shaft portion 14 may take a number of different configurations. In the embodiment shown in FIG. 4A, a shaft portion 14A comprises a pair of tubes 14A1, 14A2 that are joined together in parallel. Tubes 14A1, 14A2 may be welded or affixed in another suitable manner together at certain spaced apart points or continuously along their length. Tubes 14A1, 14A2 may be made of stainless steel or other suitable material. The two-tube configuration in FIG. 4A allows shaft portion 14A to bend more easily in a plane extending between the two tubes than in a plane of the two tubes.

Figure 4B:
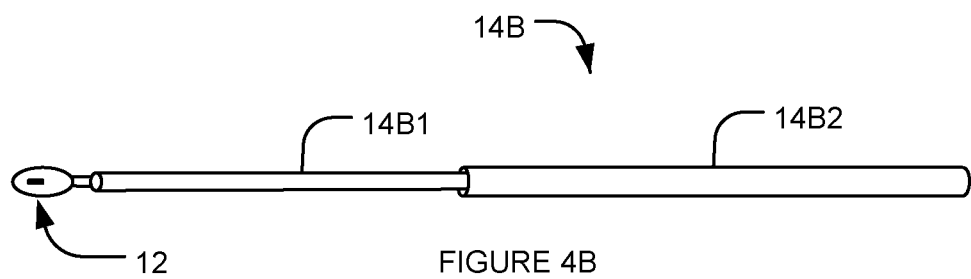
FIG. 4B illustrates a shaft portion comprising telescoping tubes.

In the embodiment shown in FIG. 4B, a shaft portion 14B comprises a pair of tubes 14B1, 14B2 that are coupled together in a concentric fashion. Tube 14B1 has a smaller diameter than tube 14B2 and is insertable and movable in tube 14B2. Tube 14B1 is distal to tube 14B2. Tube 14B1 may be more flexible than tube 14B2.

Figure 5A:
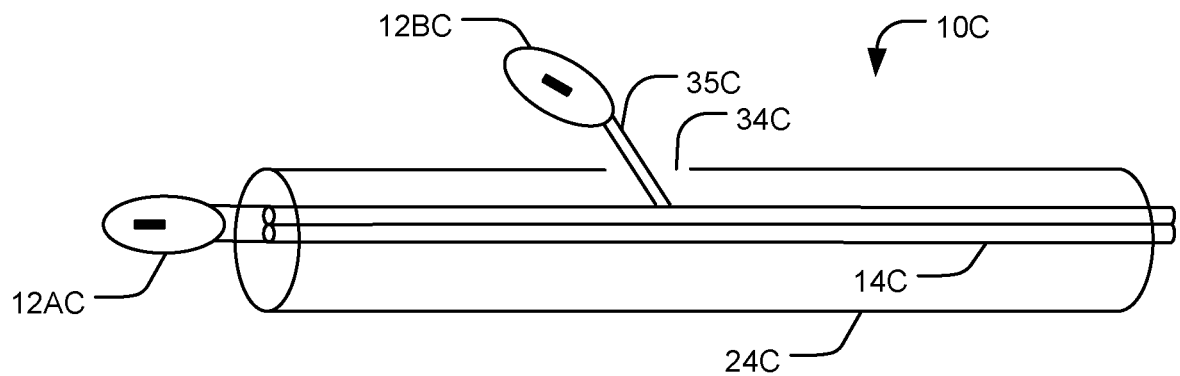
FIGS. 5A and 5B are schematic views of a nerve stimulation apparatus according to an example embodiment of the invention.
Figure 5B:
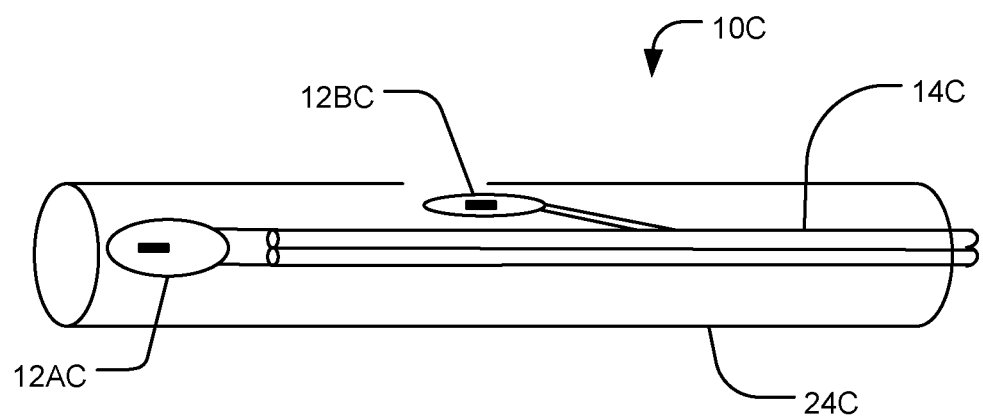

FIGS. 5A and 5B are schematic views of a nerve stimulation apparatus 10C according to an example embodiment of the invention (in a deployed configuration and a retracted configuration respectively). In the FIGS. 5A and 5B embodiment, electrode structure 12AC is coupled to a distal end of shaft portion 14C, and electrode structure 12BC is coupled to a mid-portion of shaft portion 14C. The coupling between electrode structure 12B and shaft portion 14C may comprise a spring mechanism 35C. Electrode structure 12AC is retractable and extendable through a distal opening of tubular member 24C. Electrode structure 12BC is retractable and extendable through a side opening 34C of tubular member 24C.

Figure 6A:
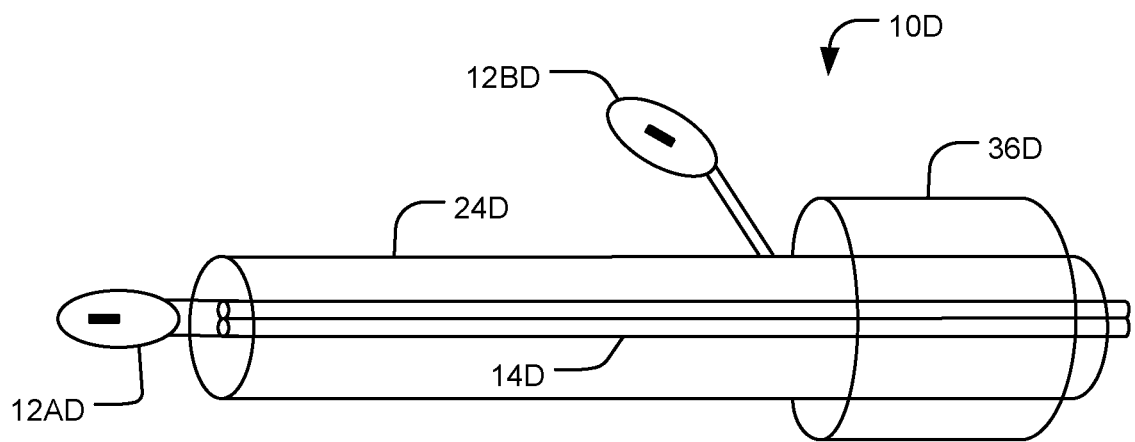
FIGS. 6A and 6B are schematic views of a nerve stimulation apparatus according to another example embodiment of the invention.
Figure 6B:
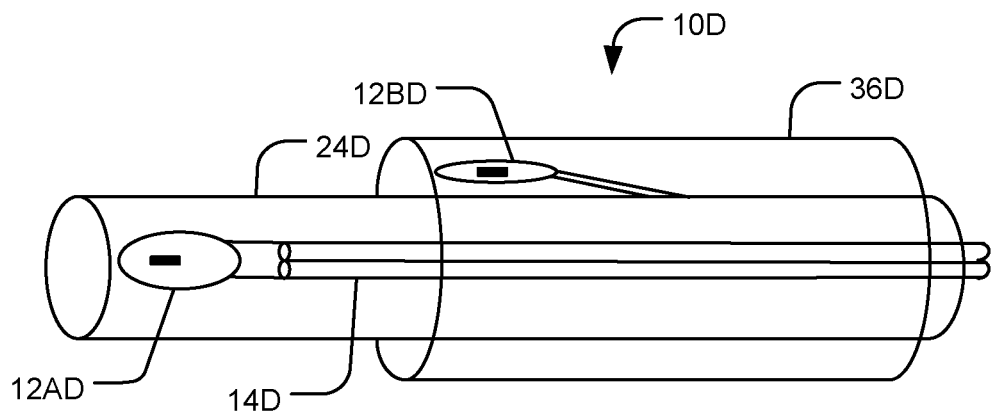

FIGS. 6A and 6B are schematic views of a nerve stimulation apparatus 10D according to another example embodiment of the invention. In the embodiment shown in FIGS. 6A and 6B, nerve stimulation apparatus 10D comprises a first tubular member 24D and a second tubular member 36D. Electrode structure 12AD is coupled to a distal end of shaft portion 14D. However, electrode structure 12BD is disposed on first tubular member 24D. Also, first tubular member 24D passes through second tubular member 36D and electrode structure 12BD is retractable into second tubular member 36D. First and second tubular members 24D, 36D may be assembled in a telescoping fashion. Second tubular member 36D has a diameter greater than the diameter of first tubular member 24D. Second tubular member 36D is typically shorter than first tubular member 24D. The position of electrode structures 12AD, 12BD may be controlled independently from one another via shaft portion 14D and tubular member 24D respectively.

Figure 7A:
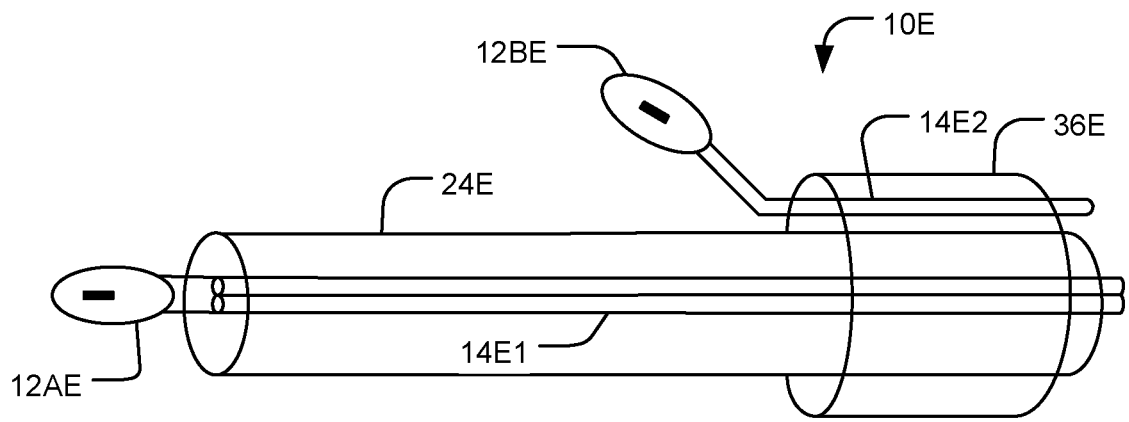
FIGS. 7A and 7B are schematic views of a nerve stimulation apparatus according to another example embodiment of the invention.
Figure 7B:
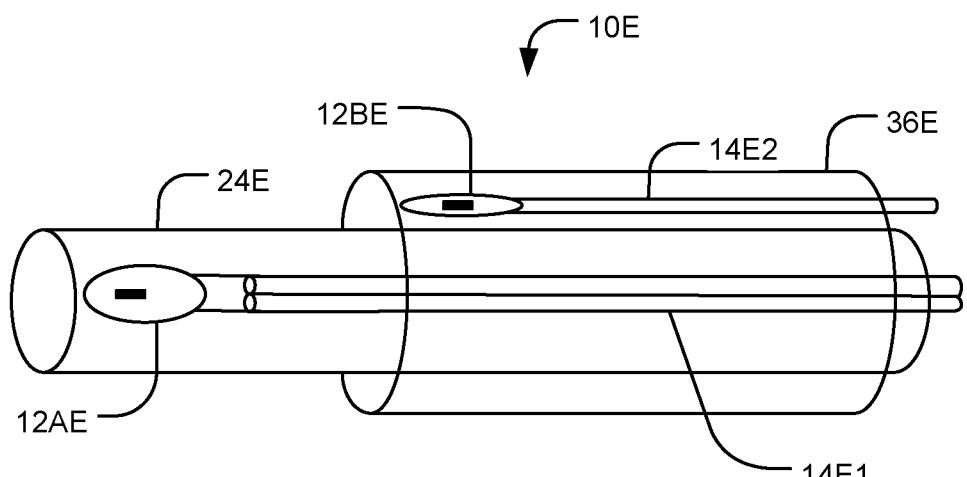

FIGS. 7A and 7B are schematic views of a nerve stimulation apparatus 10E according to another example embodiment of the invention. In the FIGS. 7A and 7B embodiment, electrode structure 12AE is coupled to a shaft portion 14E1, and electrode structure 12BE is disposed on a shaft portion 14E2 which is separate from shaft portion 14E1. Shaft portion 14E2 may be structurally different from shaft portion 14E1. Shaft portions 14E1, 14E2 may be independently controlled to deploy or retract electrode structures 12AE, 12BE, respectively. Also, first tubular member 24E passes through a second tubular member 36E. Electrode structure 12AE is retractable into first tubular member 24E. Electrode structure 12BE is retractable into second tubular member 36E. Second tubular member 36E has a diameter greater than the diameter of first tubular member 24E. Second tubular member 36E is typically shorter than first tubular member 24E.

Figure 8:
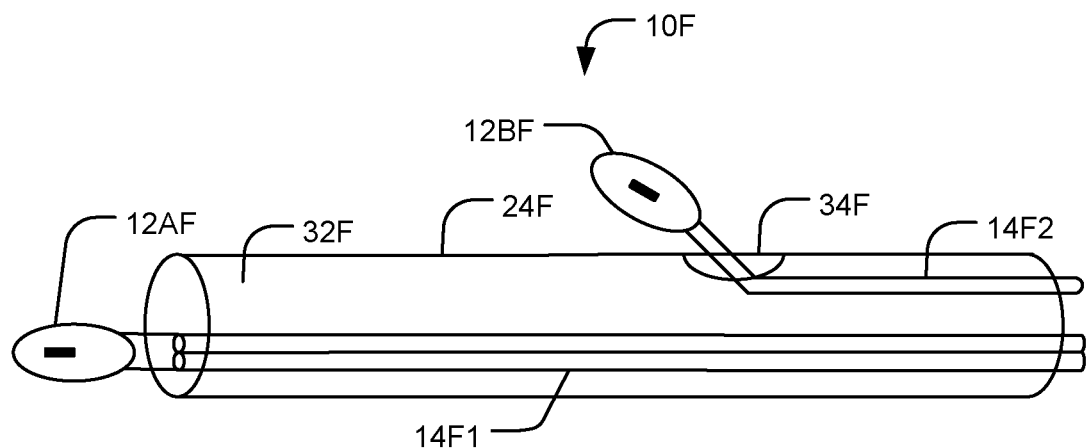
FIG. 8 schematically shows a nerve stimulation apparatus according to another example embodiment of the invention.

FIG. 8 schematically shows a nerve stimulation apparatus 10F according to another example embodiment of the invention. In the FIG. 8 embodiment, electrode structure 12AF is coupled to a shaft portion 14F1, and electrode structure 12BF is disposed on a shaft portion 14F2 which is separate from shaft portion 14F1. Shaft portion 14F2 may be structurally different from shaft portion 14F1. Shaft portions 14F1, 14F2 may be independently controlled to deploy or retract electrode structures 12AF, 12BF, respectively. Tubular member 24F comprises a single lumen 32F. Both shaft portions 14F1 and 14F2 extend inside lumen 32F. Electrode structure 12AF may extend out of a distal opening of lumen 32F. Electrode structure 12BF may extend out of a side opening 34F of tubular member 24F.

Figure 9:
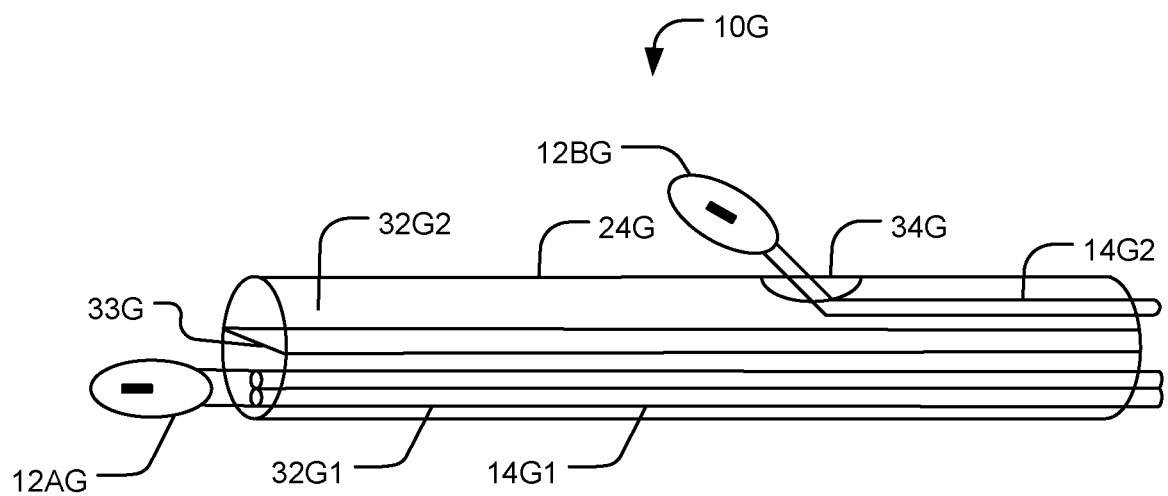
FIG. 9 schematically shows a nerve stimulation apparatus according to another example embodiment of the invention.

FIG. 9 schematically shows a nerve stimulation apparatus 10G according to another example embodiment of the invention. Apparatus 10G is similar to apparatus 10F except that tubular member 24G of apparatus 10G comprises two lumens 32G1 and 32G2. The two lumens 32G1 and 32G2 are separated by a partition 33G. Shaft portion 14G1 extends in lumen 32G1 and electrode structure 12AG extends out of a distal opening of lumen 32G1. Shaft portion 14G2 extends in lumen 32G2 and electrode structure 12BG extends out of a side opening 34G of lumen 32G2.

Figure 10A:
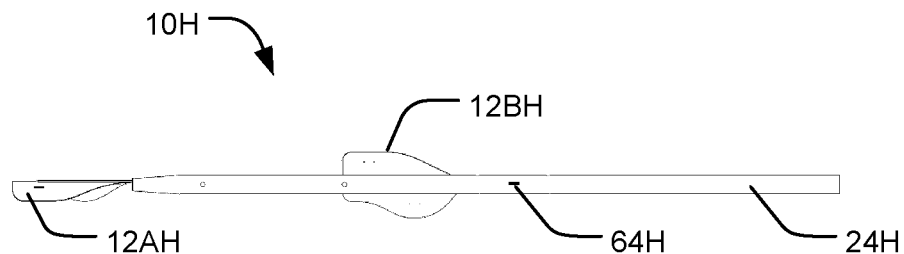
FIG. 10A is a side view of a nerve stimulation apparatus according to another example embodiment of the invention.
Figure 10B:
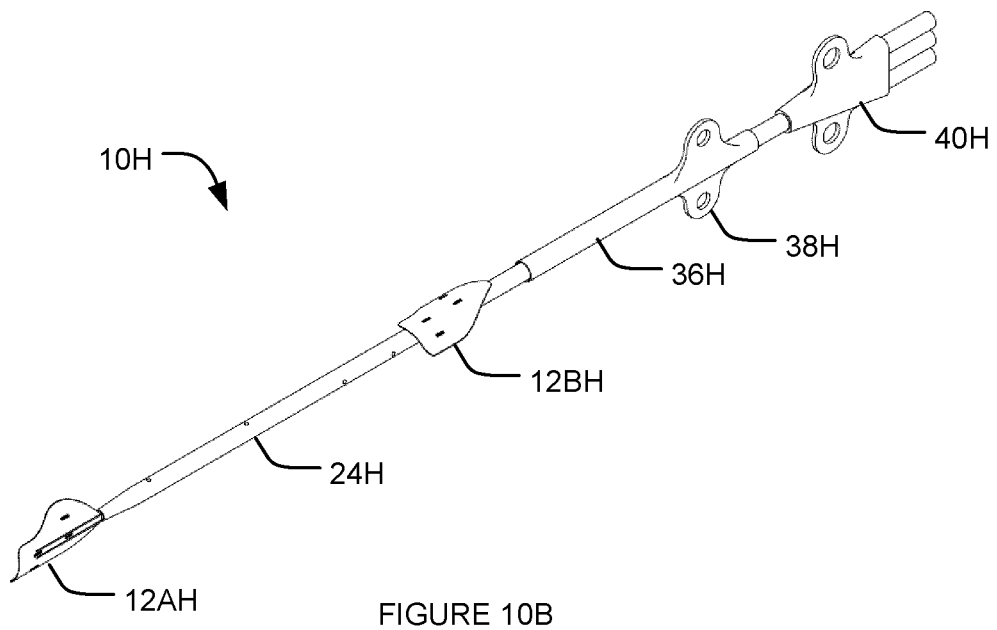
FIG. 10B is an isometric view of the apparatus of FIG. 10A in combination with an introducer and a hub.
Figure 10C:
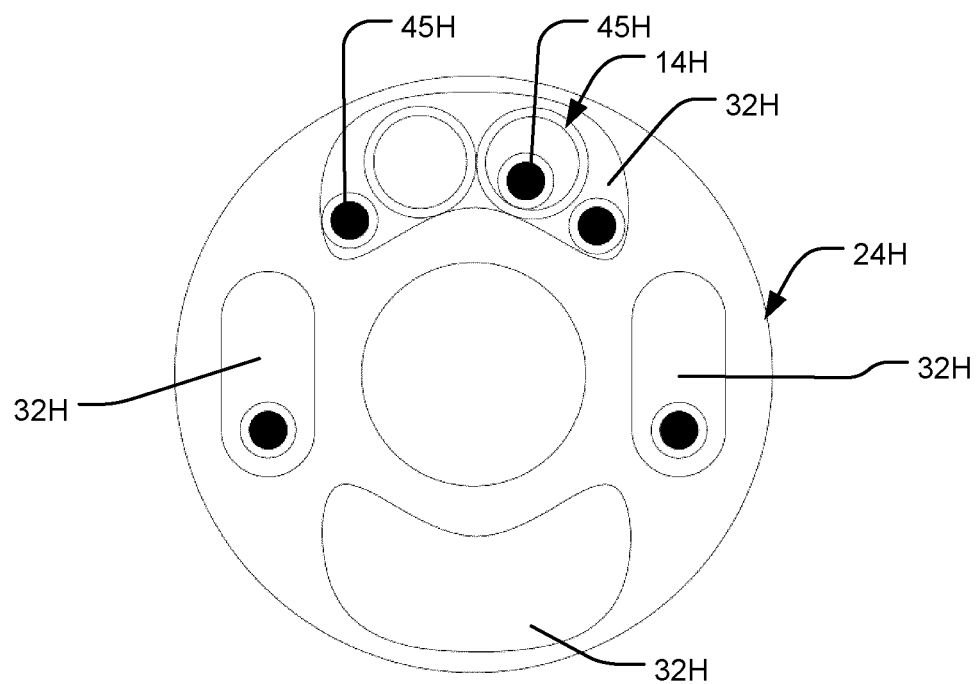
FIGS. 10C and 10D are examples of alternative cross-sectional views of the apparatus of FIG. 10A.
Figure 10D:
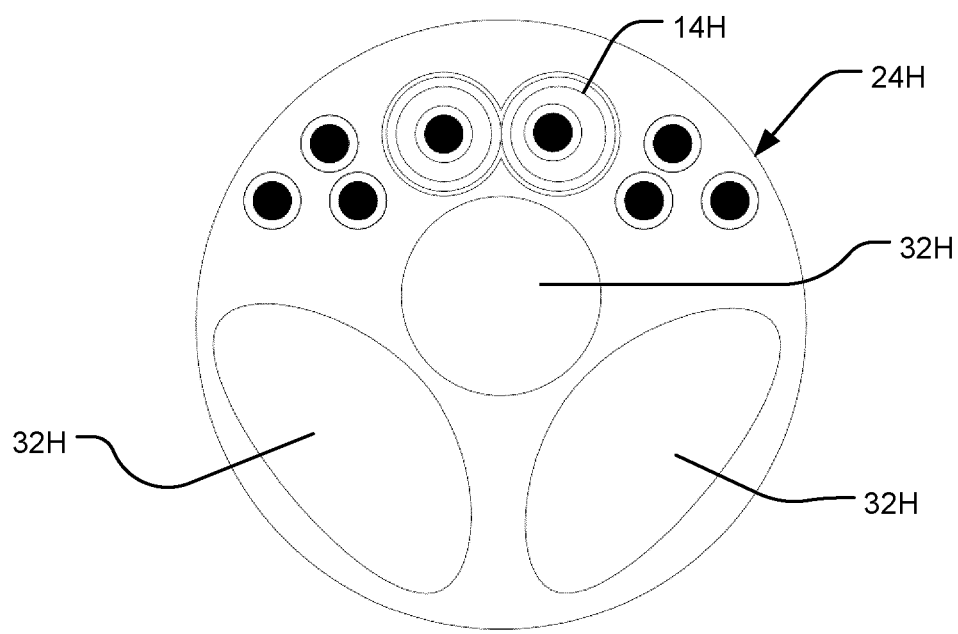

FIG. 10A is a side view of a nerve stimulation apparatus 10H according to an example embodiment of the invention. FIG. 10B is an isometric view of apparatus 10H in combination with an introducer 38H and a hub 40H. FIGS. 10C, 10D are possible cross-sectional views of apparatus 10H. Nerve stimulation apparatus 10H comprises electrode structures 12AH, 12BH, and a tubular member 24H.

Nerve stimulation apparatus 10H may be coupled to an introducer 38H and a hub 40H. This may be done during use to facilitate entry of the nerve stimulation apparatus into a patient's blood vessel. It should be noted that other types of introducers and/or hubs different from the ones shown in FIG. 10B may also be used in conjunction with nerve stimulation apparatus 10H. Electrode structure 12AH is connected to a shaft portion 14H which extends inside tubular member 24H. Electrode structure 12BH is disposed on first tubular member 24H. The distance between electrode structure 12AH and 12BH may be in the range of 5-10 cm for example. The distance between electrode structure 12BH and the distal end of introducer 38H may be in the range of 0-5 cm for example.

Tubular member 24H is partially received in tubular member 36H of introducer 38H. When nerve stimulation apparatus 10H is applied to a patient, hub 40H and the wing portion of introducer 38H stay outside of the patient. Introducer 38H and/or hub 40H may comprise holes for suture. In their deployed configuration, electrode structures 12AH and 12BH have a transverse dimension that is greater than the transverse dimension of tubular member 24H. Apparatus 10H comprises a thermistor 64H or other temperature sensor.

Tubular member 24H may comprise a multi-lumen catheter. FIGS. 10C, 10D show possible cross sections of tubular member 24H. Tubular member 24H may have 1, 2, 3, 4, 5, or more lumens 32H. Shaft portion 14H and leads 45H may run inside one or more of the lumens 32H. Leads 45H may also run inside the bore of shaft portion 14H.

Figure 11A:
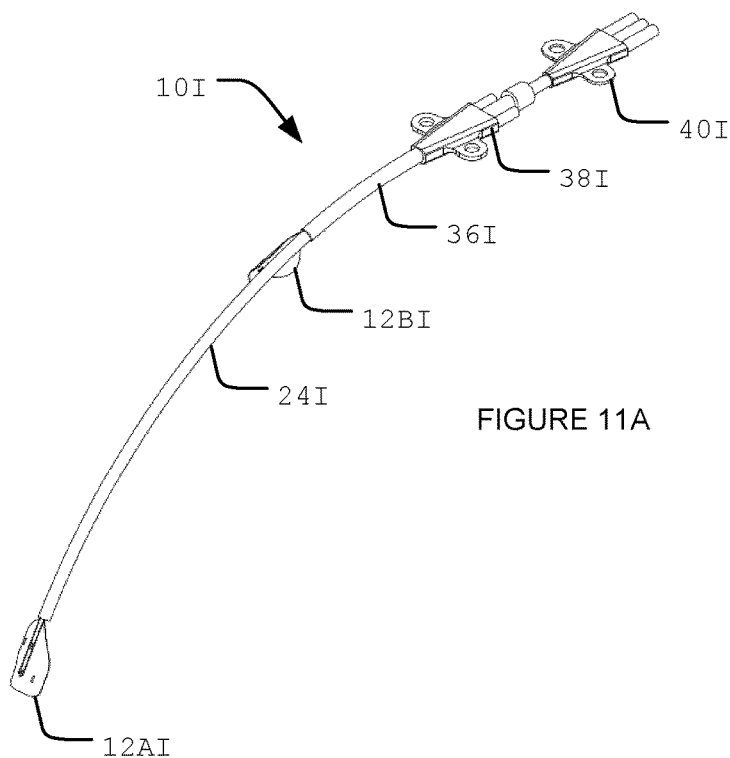
FIGS. 11A and 11B show a nerve stimulation apparatus in combination with an introducer and a hub according to an example embodiment of the invention.
Figure 11B:
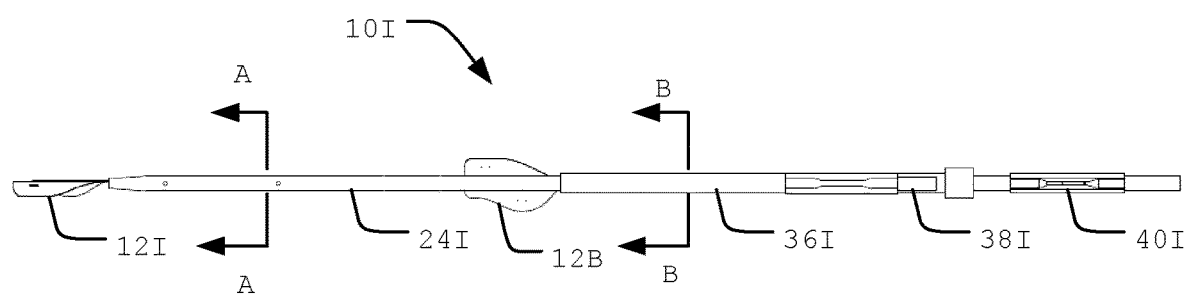
Figure 11C:
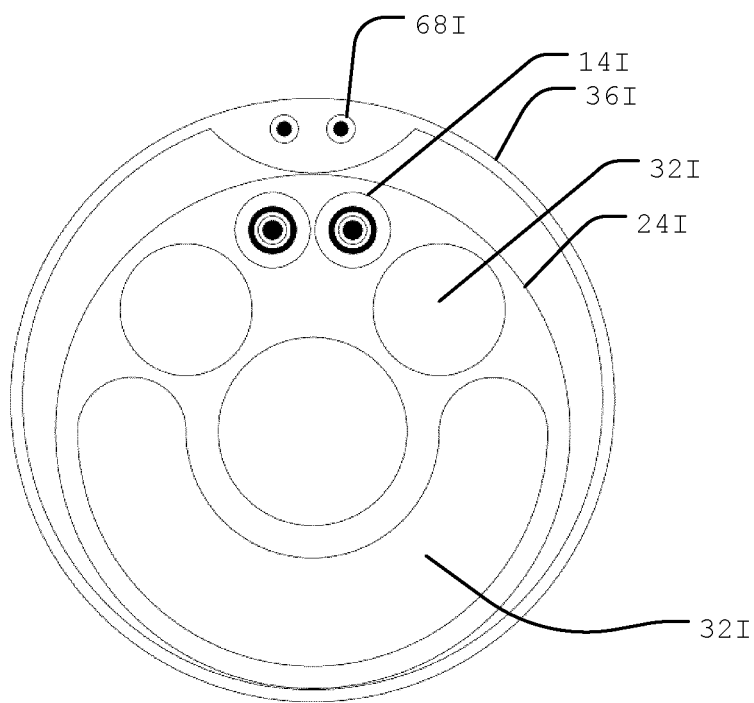
FIGS. 11C and 11D are cross sectional views of nerve stimulation apparatus along lines B-B and A-A respectively shown in FIG. 11B.
Figure 11D:
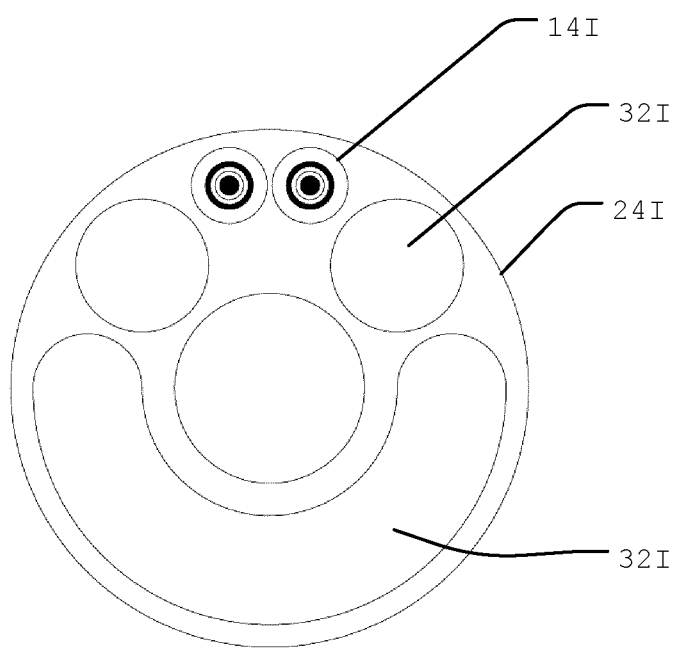

FIGS. 11A and 11B show a nerve stimulation apparatus 10I in combination with an introducer 38I and a hub 40I according to an example embodiment of the invention. FIGS. 11C and 11D are cross sectional views of nerve stimulation apparatus 10 along lines B-B and A-A respectively in FIG. 11B. Nerve stimulation apparatus 10I comprises a first tubular member 24I, a second tubular member 36I, an introducer 38I, a hub 40I, a first electrode structure 12AI, a second electrode structure 12BI, a first shaft portion 14I (not visible) and a second shaft portion 68I (not visible). Electrode structure 12AI is attached to a distal end of first shaft portion 14I. First shaft portion 14I is visible in FIGS. 11C and 11D (in cross section). Electrode structure 12AI is retractable into the distal end of tubular member 24I. Electrode structure 12BI is attached to second shaft portion 68I. Electrode structure 12BI is extendable out of the distal end of second tubular member 36I and is retractable into the distal end of tubular member 36I. Second shaft portion 68I is visible in FIG. 11C (in cross section). First tubular member 24I is longer than second tubular member 36I and passes through second tubular member 36I. First tubular member 24I comprises a plurality of lumens 32I, and second tubular member 36I surrounds the multi-lumen first tubular member 24I. Because electrode 12AI and 12BI are attached to two separate shaft portions 14I and 68I, respectively, electrode structures 12AI and 12BI can be independently controlled from outside the body.

Figure 12:
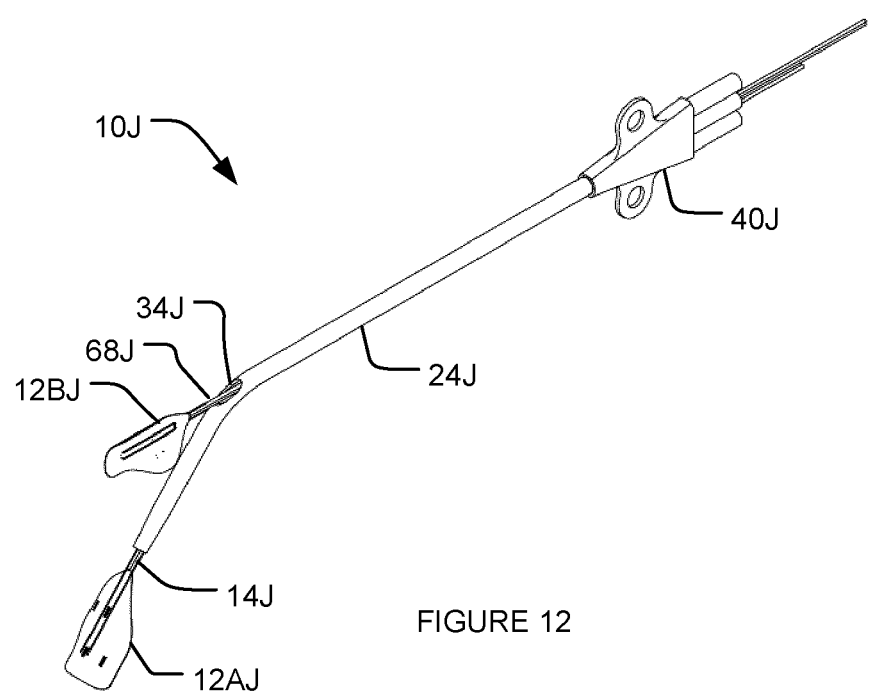
FIG. 12 shows a nerve stimulation apparatus according to an example embodiment of the invention.

FIG. 12 shows a nerve stimulation apparatus 10J according to an example embodiment of the invention. Apparatus 10J comprises a tubular member 24J. Electrode structure 12AJ extends out of the distal end of tubular member 24J whereas electrode 12BJ extends out of an opening 34J on tubular member 24J. Electrode structure 12AJ is attached to shaft portion 14J and electrode structure 12B is attached to shaft portion 68J. Shaft portions 14J and 68J are both inside tubular member 24J. Electrode structures 12AJ and 12BJ can be independently controlled from outside the body.

Figure 13A:
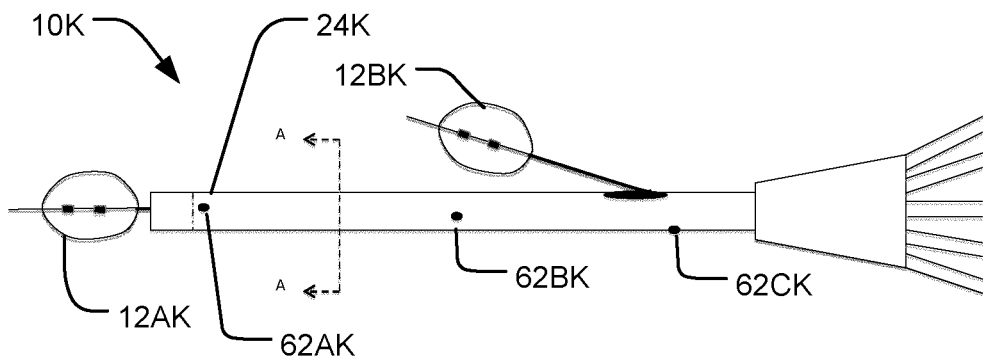
FIG. 13A shows a nerve stimulation apparatus according to an example embodiment of the invention that provides a five-lumen catheter.
Figure 13B:
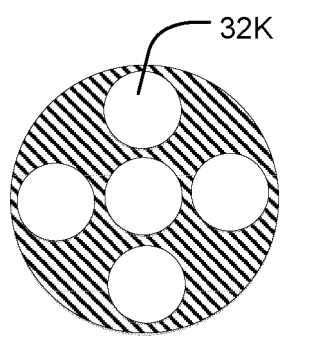
FIGS. 13B-13E show some possible cross sections of the apparatus of FIG. 13A taken at line A-A in FIG. 13A.
Figure 13C:
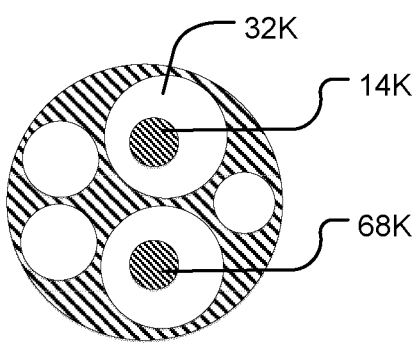
Figure 13D:
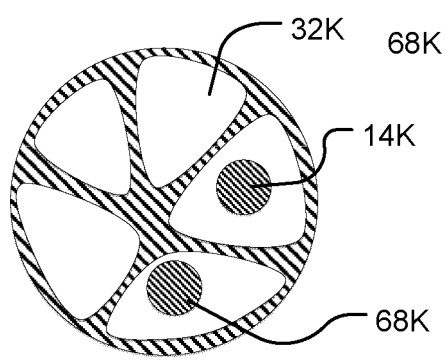
Figure 13E:
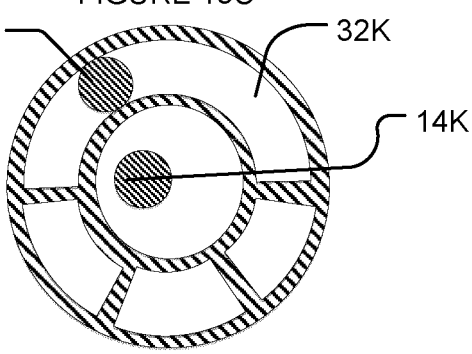

FIG. 13A shows a nerve stimulation apparatus 10K. In this embodiment, tubular member 24K has five lumens 32K. FIGS. 13B-13E show some possible cross sections of tubular member 24K taken at line A-A in FIG. 13A. Three lumens 32K may be used for drug infusion and are in fluid communication with openings 62AK, 62BK, 62CK located in a proximal, middle and distal portion of tubular member 24K. One lumen contains shaft portion 14K which is coupled to electrode structure 12AK. One lumen contains shaft portion 68K which is coupled to electrode structure 12BK. In FIG. 13B, each of the five lumens has the same size and has a circular cross section. In FIG. 13C, the lumens have different sizes, but all have circular cross sections. In FIG. 13D, the lumens have different sizes and non-circular cross sections. In FIG. 13E, the lumens have different sizes and are a mix of circular and non-circular cross sections.

FIG. 14A is another embodiment of a nerve stimulation apparatus 10L. FIGS. 14B and 14C show some possible cross sections of tubular member 24L in the FIG. 14A embodiment. In the FIG. 14A embodiment, tubular member 24L has three lumens 32L. One lumen 32L contains shaft portion 14L which is coupled to electrode structure 12AL. One lumen 32L contains shaft portion 68L which is coupled to electrode structure 12BL. One lumens may be used for drug infusion to opening 62L located in a middle portion of tubular member 24L. In FIG. 14B, each of the three lumens has the same size and has a circular cross section. In FIG. 14C, the lumens have non-circular cross sections.

Figure 15:
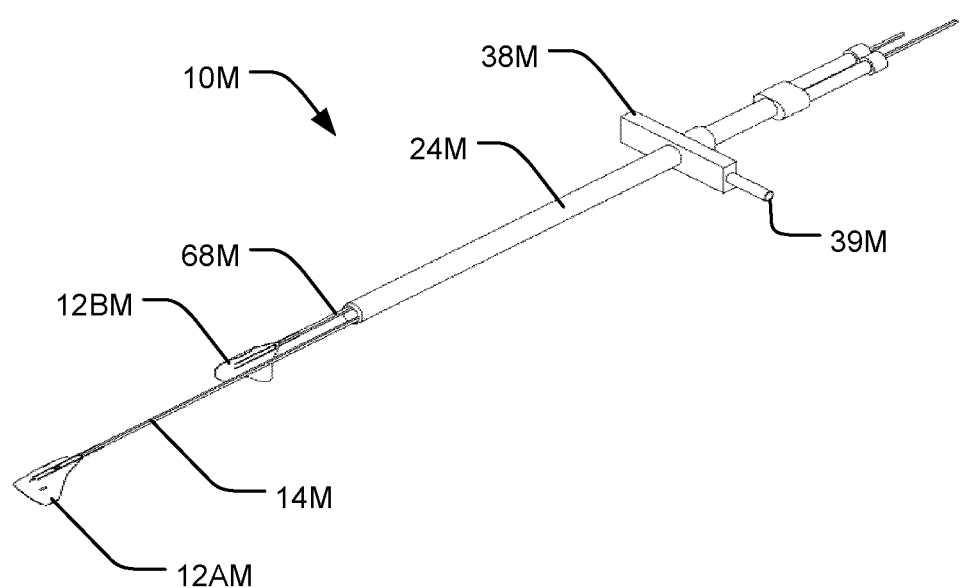
FIG. 15 shows a nerve stimulation apparatus.

FIG. 15 shows a nerve stimulation apparatus 10M. Apparatus 10M comprise a tubular member 24M. The proximal end of tubular member 24M is coupled to introducer 38M. Introducer 38M has a side port 39M. Both electrode structures 12AM, 12BM extend out of a distal opening of tubular member 24M. Electrode structure 12AM is coupled to shaft portion 14M. Electrode structure 12BM is coupled to shaft portion 68M. Electrode structures 12AM and 12BM can be independently controlled.

Figure 16:
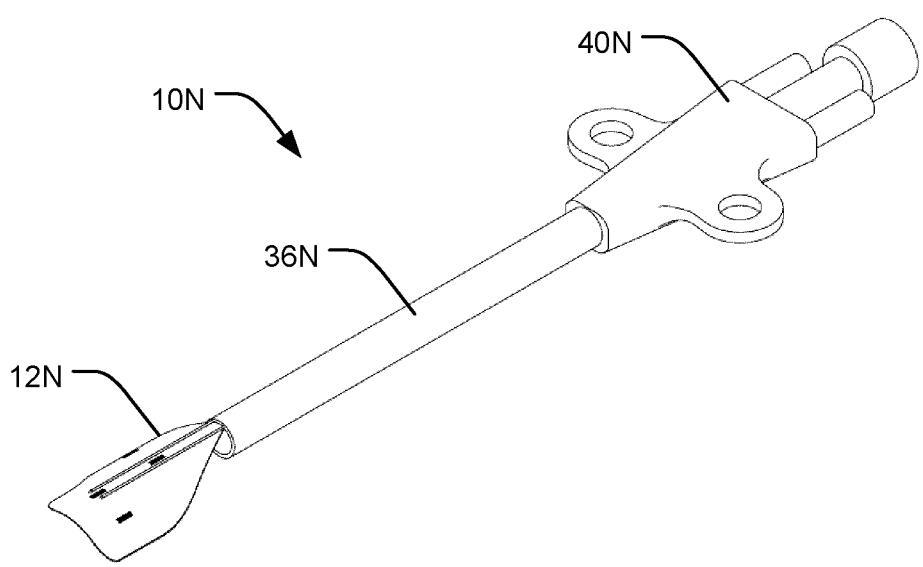
FIG. 16 shows a nerve stimulation apparatus.

FIG. 16 shows a nerve stimulation apparatus 10N. Nerve stimulation apparatus 10N comprises a tubular member 36N, an electrode structure 12N and a shaft portion 14N (not visible). Electrode structure 12N extends out of a distal opening of tubular member 36N. Shaft portion 14N is inside tubular member 36N. Tubular member 36N may be a cannula or catheter-type tubular member. The length of tubular member 36N is sufficiently long to enter the vessel by about 1 cm such that nerve stimulation apparatus 10N is suitable for stimulating the left phrenic nerve when inserted into a patient's LSV and left BCV.

Figure 17:
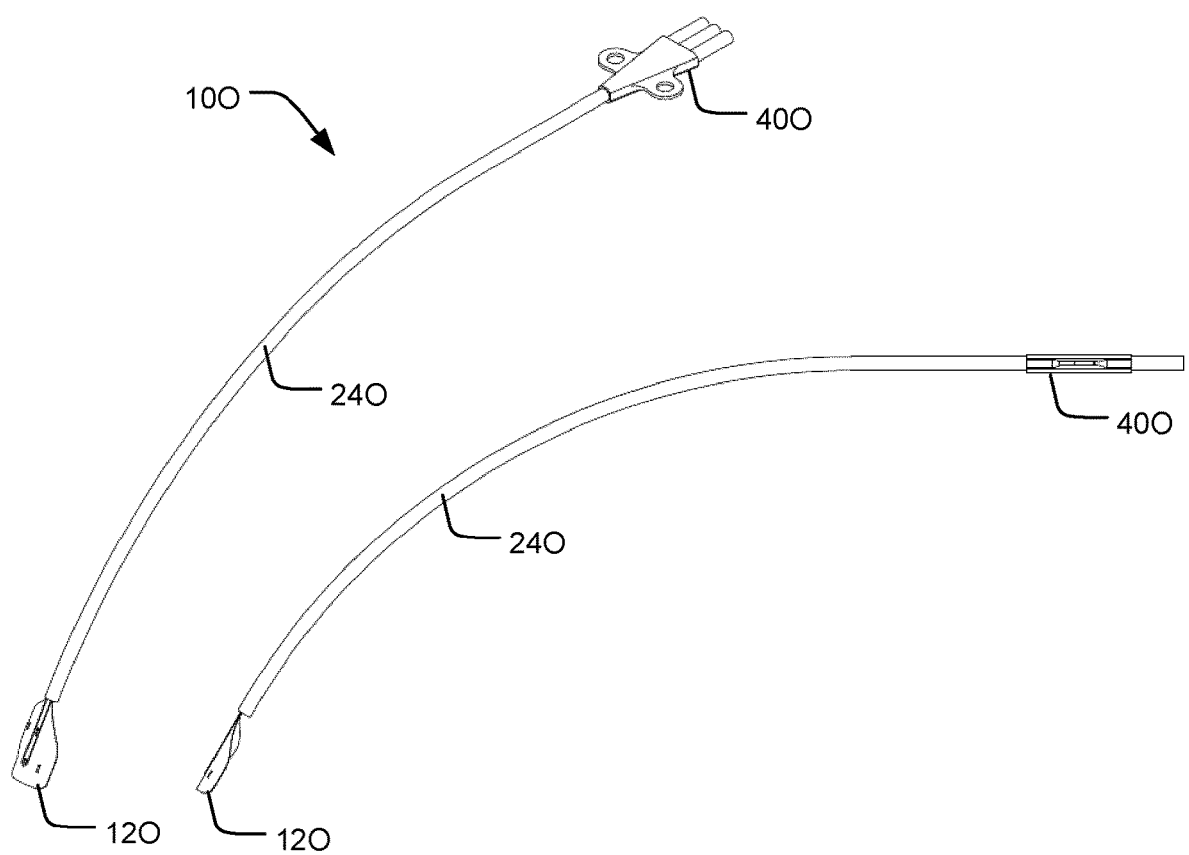
FIG. 17 shows a nerve stimulation apparatus.

FIG. 17 shows a nerve stimulation apparatus 10O. Nerve stimulation apparatus 10O comprises a tubular member 24O, an electrode structure 12O and a shaft portion 14O (not visible). Electrode structure 12O is attached to a distal end of shaft portion 14O. Shaft portion 14O is not visible in FIG. 17 because shaft portion 14O is inside tubular member 24O. Tubular member 24O may be a catheter-type tubular member. The length of tubular member 24O may be 16-20 cm so that nerve stimulation apparatus 10O is suitable for stimulating the right phrenic nerve when inserted into a patient's LSV, left BCV and then enters SVC. It should be noted that apparatus 10N, 10O may be used in combination to stimulate both left and right phrenic nerves at the same time.

Figure 18A:
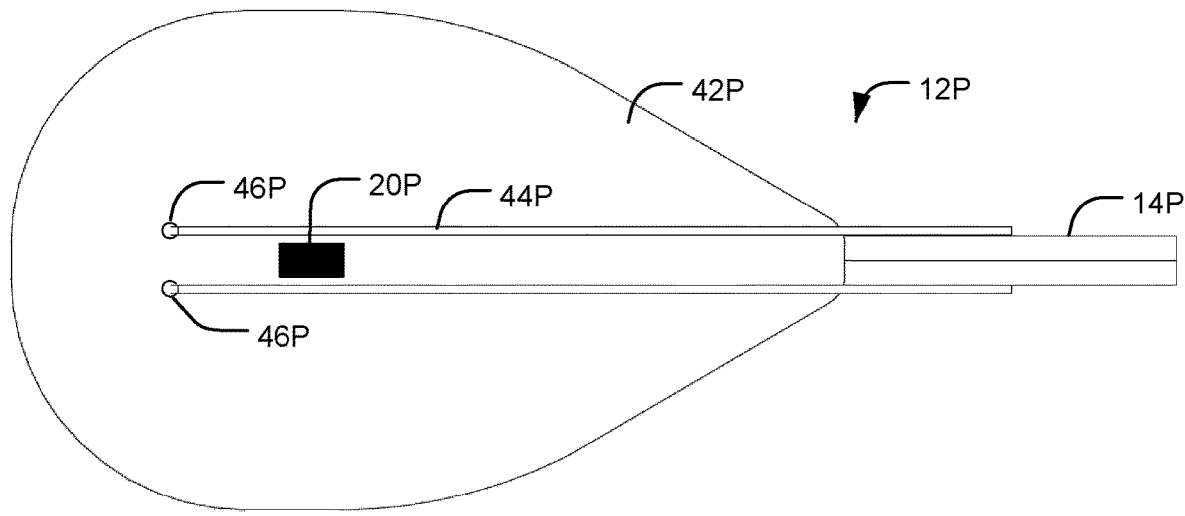
FIGS. 18A, 18B show an electrode structure according to an example embodiment of the invention.
Figure 18B:
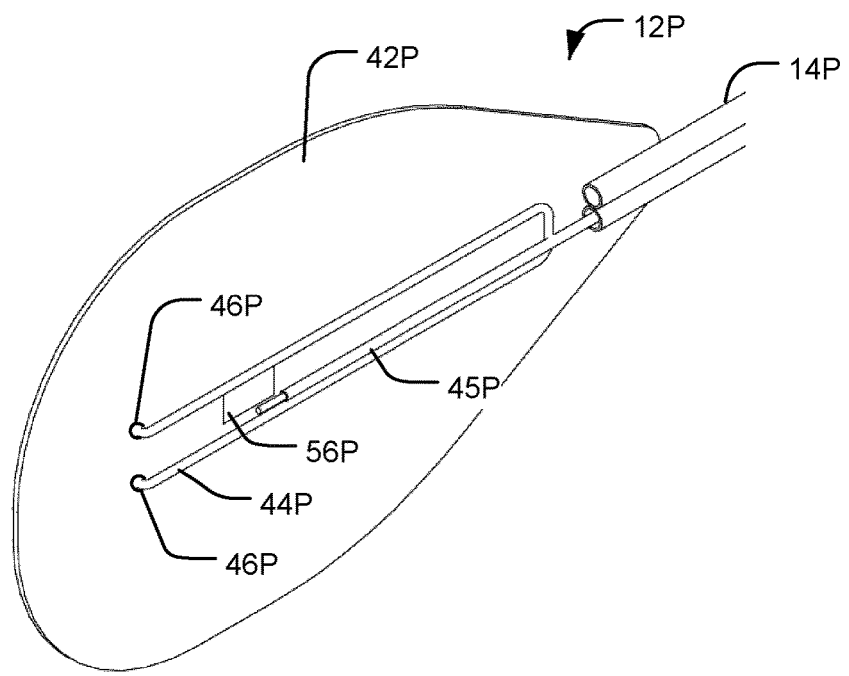

FIGS. 18A, 18B show an electrode structure 12P according to an example embodiment of the invention. FIG. 18A is a top plan view of electrode structure 12P. FIG. 18B is a bottom perspective view of electrode structure 12P. Electrode structure 12P comprises at least one electrode 20P and an insulating pad 42P. Pad 42P may be resiliently flexible. When electrode structure 12P is not confined inside a tubular member, pad 42P can automatically spring open to take a desired shape. When electrode structure 12P springs open, electrode structure 12P may have a dimension that is greater than the transverse dimension of the tubular member. To retrieve electrode structure 12P into a tubular member, electrode structure 12P can be collapsed and/or pulled back into the tubular member by pulling shaft portion 14P which is coupled to electrode structure 12P. Electrode 20P may be supported on pad 42P, but this is not mandatory. Pad 42P has a petal or leaf-like shape, although pad 42P may be of any other suitable shape. Pad 42P may be an insulating pad, thereby insulating electrode 20P from the blood in a blood vessel. Pad 42P may be made of an insulating material or materials. Suitable materials for making pad 42P include, without limitation, PTEF, silicone, PET, and nylon. Pad 42P may present a high-impedance to the flow of electrical current and therefore reduces the amount of current flowing through the blood when electrode structure 12P is deployed in a blood vessel.

It is not mandatory that pad 42P have an extremely high electrical resistance. It is sufficient if pad 42P has a resistance to the flow of electricity through pad 42P that is significantly greater than that presented by the blood in blood vessel V. Blood typically has a resistivity of about 120 to 190 Ωcm. In example embodiments, the blood in a blood vessel may provide an electrical resistance between closely-spaced electrical contacts that is inversely proportional to the dimensions of the lumen of the blood vessel. In large blood vessels the longitudinal electrical resistance between reasonable closely-spaced contacts can be a few tens of ohms for example. Pad 42P preferably provides an electrical resistance of at least a few hundred ohms, preferably a few kilo ohms or more to the flow of electrical current through the thickness of pad 42P. Pad 42P could have electrically conductive members such as leads and the like embedded within it or electrically-conductive electrode or other features on its inner surface and still be considered to be 'insulating'.

For example, electrode 20P may be supported on pad 42P. Pad 42P can be rolled up and retracted into the tubular member to facilitate insertion or retrieval of electrode structure 12P within a blood vessel. When electrode structure 12P is deployed, pad 42P can spring open to take a shape that has a curvature that generally conforms to the wall of a blood vessel. This helps to bring electrode 20P which is on a side of pad 42P to be in close proximity of the blood vessel wall. Blood flow in the blood vessel may also assist in deploying electrode structure 12P and pressing pad 42P against the walls of a blood vessel. It should be noted that electrode structure 20P does not need to be fixed or fastened to the blood vessel wall, but rather can float inside the blood vessel against the wall.

In the embodiment of FIGS. 18A, 18B, electrode structure 12P also comprises a wire 44P which is connected to shaft portion 14P. Wire 44P passes through apertures 46P in pad 42P, thereby holding pad 42P in place. Wire 44P may provide structural support to pad 42P. Additionally, wire 44P may optionally serve as a ground electrode or a reference electrode. In FIG. 18B, a lead 45P extends from a bore in shaft portion 14P to a backside 56P of electrode 20P. Lead 45P may be coated with an insulating material (e.g., Teflon™ or other suitable insulating material). Sensors such as a thermistor, an oxygen sensor, and/or $CO_2$ sensor (not shown) may be supported on electrode structure 12P. In some embodiments, electrode structures 12P may be used for plethysmography.

In the illustrated embodiment, electrode 20P is exposed on one side (e.g., the convex side, i.e., the side facing the blood vessel wall) of pad 42P. Pad 42P may, for example, comprise a reinforced silicone material. In one embodiment, pad 42P is a pad of Dacron-mesh-reinforced silicone. This material can be rolled up, has shape memory so that it tends to open up, and is resiliently flexible so that it can conform to the wall of a blood vessel. Blood flow in the blood vessel may also assist in deploying electrode structure 12P and supporting electrode structure 12P against the walls of a blood vessel.

Figure 19A:
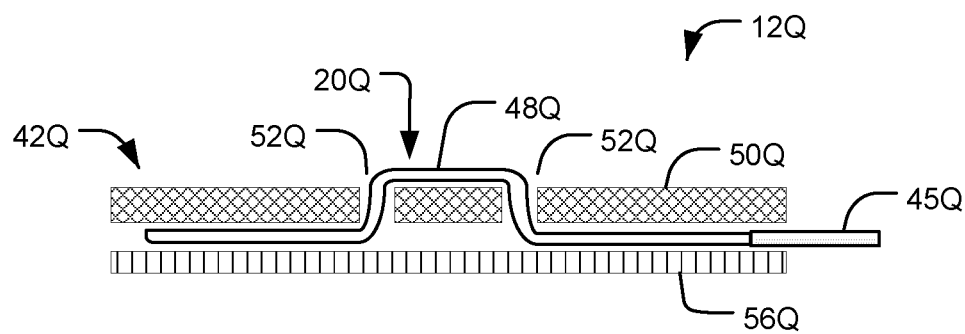
FIG. 19A shows a schematic of a cross section of an electrode structure according to one example embodiment of the invention.
Figure 19B:
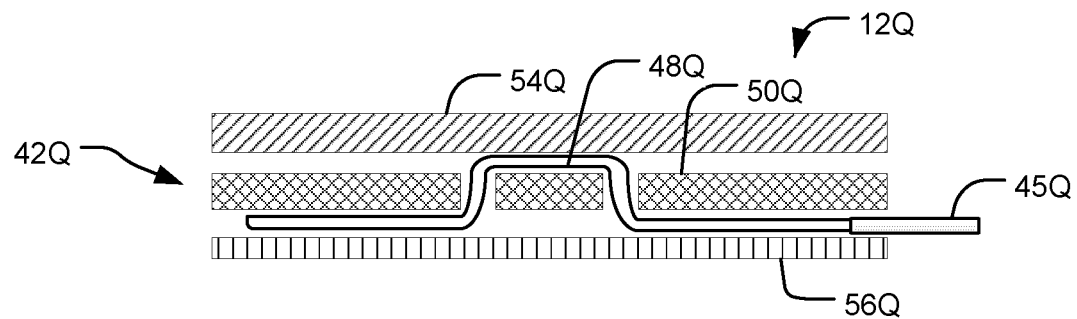
FIG. 19B shows details electrodes of the electrode structure of FIG. 19A.

FIG. 19A shows a schematic of a cross section of an electrode structure 12Q according to one example embodiment of the invention. In FIG. 19A embodiment, electrode 20Q comprises one or more ribbons 48Q of a suitable biocompatible metal. Pad 42Q on which the ribbons 48Q are supported comprises two layers. A top layer 50Q which faces the wall of the blood vessel has apertures 52Q and the ribbons 48Q pass through aperture 52Q such that a portion of the ribbons 48Q is exposed and able to contact or be in close proximity of a wall 54Q of the blood vessel. This is schematically shown in FIG. 19B. The bottom layer 56Q which faces the center of the blood vessel may be made of a suitable insulating material. Ribbons 48Q are electrically coupled to lead 45Q which is directly or indirectly coupled to a source of electricity (e.g., a stimulation generator). The bottom insulating layer 56Q may comprise a thin material such as Teflon™, polyurethane, or silicone.

The material of electrode 20Q is preferably relatively thin so that it does not make the electrode structure too stiff. For example, the electrode material may comprise metal ribbons 48Q that are 0.5 to 1 mm wide, or less than 0.5 mm wide. In other embodiments the electrodes may comprise areas of conductive polymer printed on or contained in the insulating material of the electrode structure.

Generally, the delivery of electrical stimulation to a target nerve is enhanced by:
- locating electrode 20 against the internal wall of the blood vessel at a location close to the target nerve;
- providing electrode 20 having a relatively large contact surface that can achieve a large contact area with the internal wall of the blood vessel;
- curving the contact surface of electrode 20 to roughly match the curvature of the inner face of blood vessel; and/or
- providing insulating pad 42.

Experiments conducted by the inventors have shown that it is possible to achieve a similar level of stimulation of a target nerve using insulated electrodes by applying only one third of the electric current as compared to using uninsulated electrodes. The reduced electric current can result in less damage to tissues within a patient as well as a lower risk of unintended stimulation. Additionally, selectivity for a target nerve is improved. Low current and high selectivity for a target nerve is advantageous because it avoids activating non-target nerves which may be close by. For example, it is known that the vagus nerve is typically 2-3 cm medial with respect to the phrenic nerves in humans.

Figure 20A:
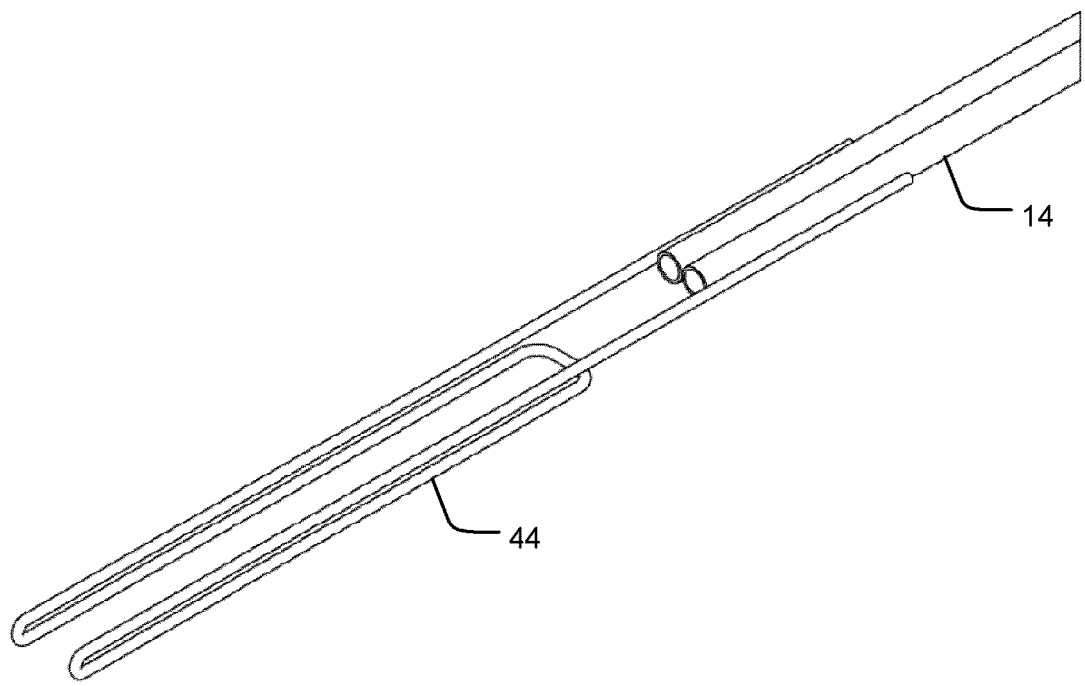
FIGS. 20A and 20B are perspective and side views of an electrode retaining wire according to one example embodiment.
Figure 20B:
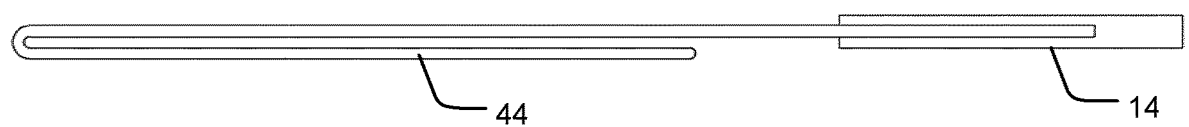

FIGS. 20A and 20B are perspective and side views of wire 44P according to one example embodiment. Wire 44P is connected to shaft portion 14P. Wire 44P may form a hair-pin configuration, extending from shaft portion 14P on one side of pad 42P (not shown in FIGS. 20A and 20B), passing through apertures 46P in pad 42P to the other side of pad 42P and then extending in the opposite direction.

Where shaft portion 14P comprises stainless steel tube(s), the wire 44P may, for example, be welded or otherwise attached to the stainless steel tube(s). Wire 44P may comprise a loop of 0.010 inch stainless steel (for example Elgiloy™). The wire of the loop may pass through apertures 46P in the insulating pad 42P on which electrode(s) 20P are supported as shown in FIGS. 18A, 18B. This positively retains pad 42P in place. Wire 44P may be passed through apertures 46P before being affixed to shaft portion 14P. In some embodiments, wire 44P provides one of a plurality of electrodes for monitoring bioelectrical activity and/or delivering electrical stimulation.

Figure 21A:
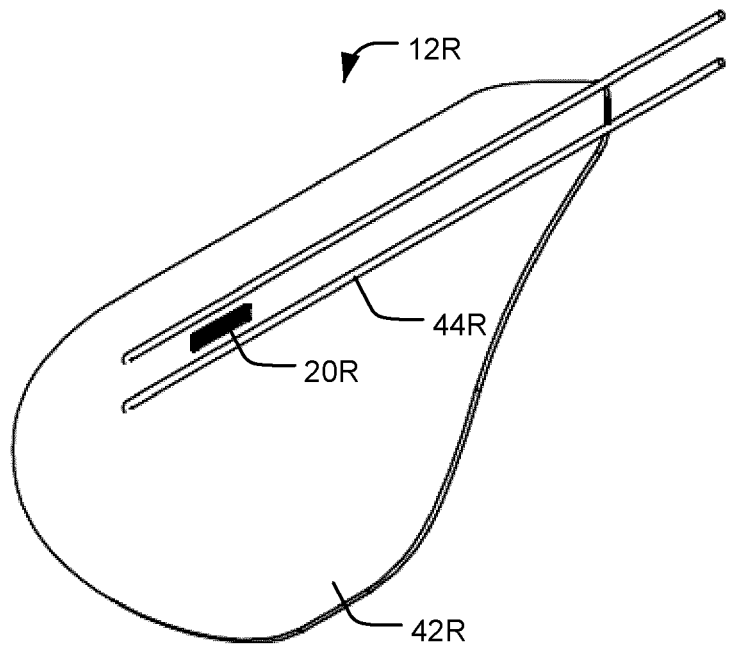
FIGS. 21A, 21B are top and bottom perspective views of an electrode structure.
Figure 21B:
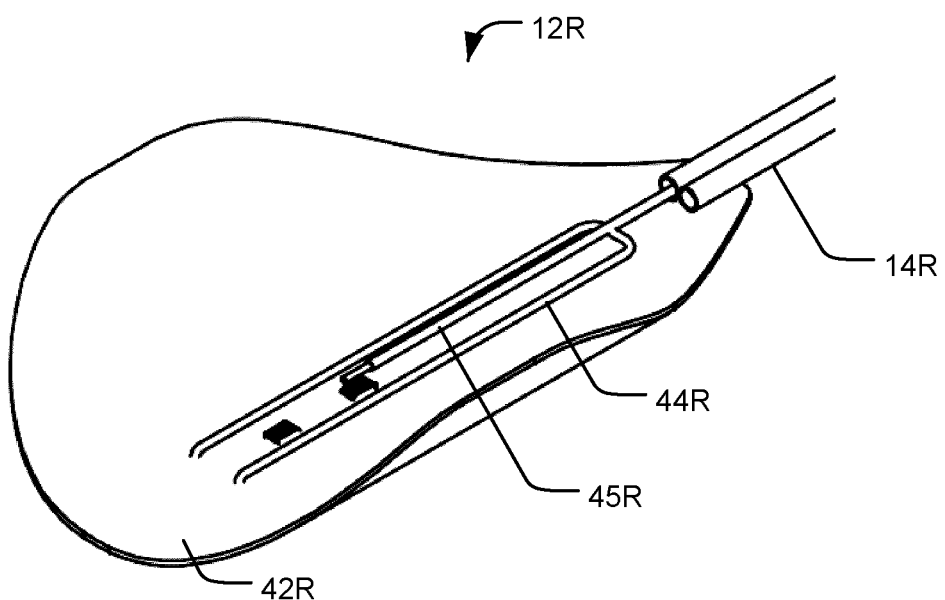

FIGS. 21A, 21B are top and bottom perspective views of an electrode structure 12R. Electrode structure 12R is similar to electrode structure 12P. In FIGS. 21A, 21B, pad 42R is flexible and partially rolled-up, and electrode 20R is located on the convex side of pad 42R.

Figure 22:
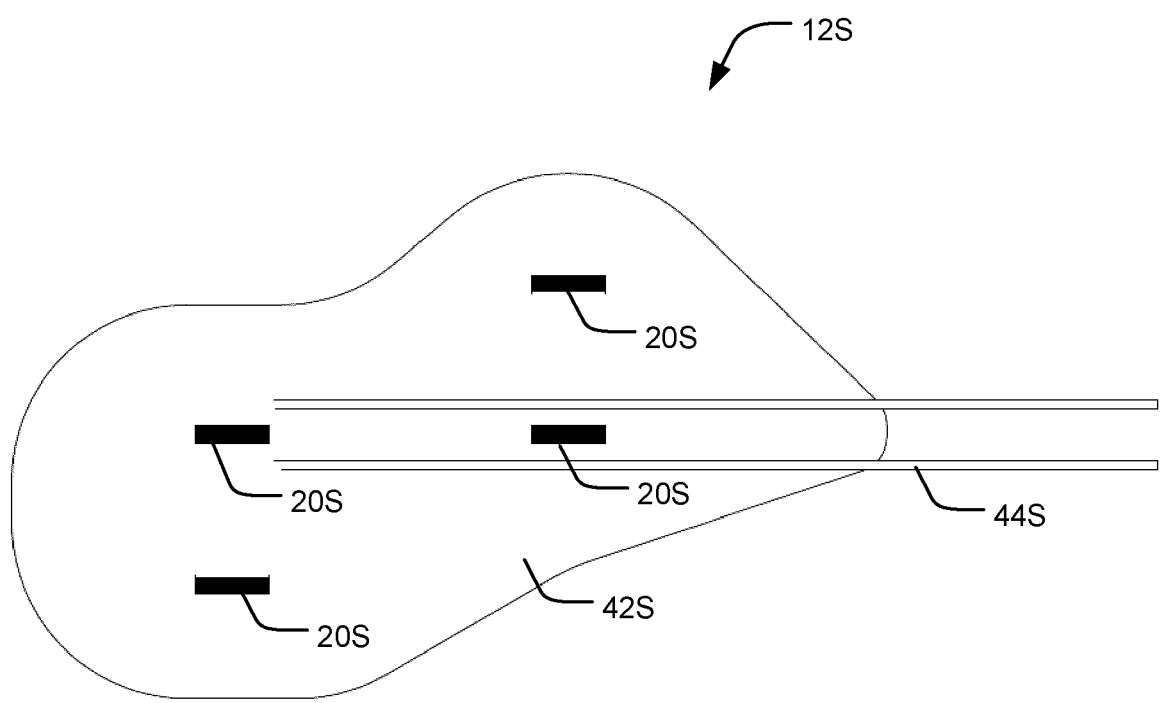
FIG. 22 shows an electrode structure according to one example embodiment.
Figure 23A:
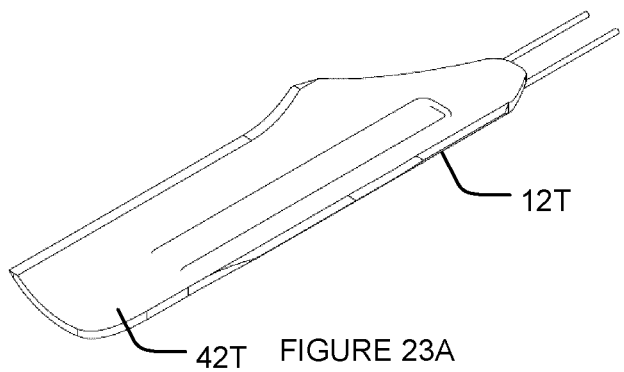
FIGS. 23A-23E show how an example electrode structure may be rolled up and retracted into a tubular member.
Figure 23B:
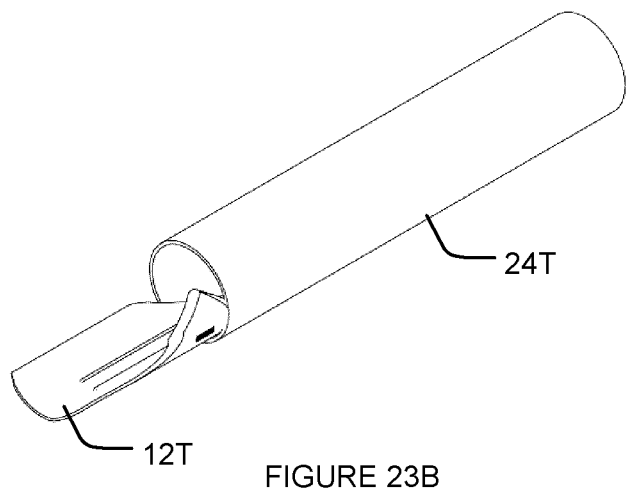
Figure 23C:
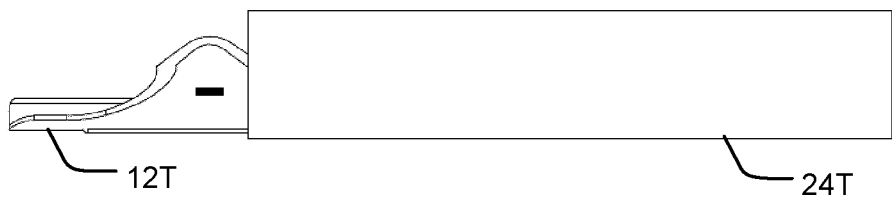
Figure 23D:
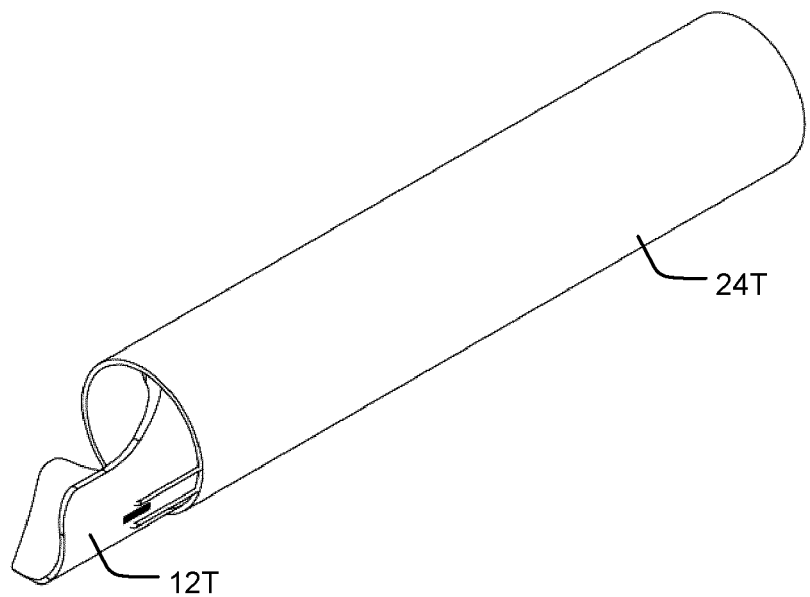
Figure 23E:
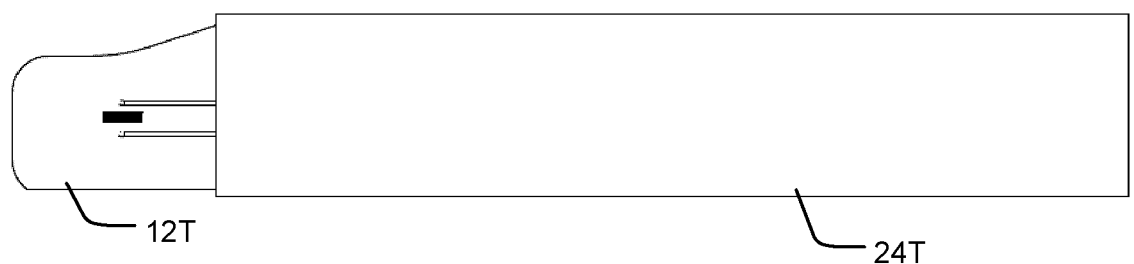

FIG. 22 shows an electrode structure 12S according to one example embodiment. As shown in FIG. 22, pad 42S of electrode structure 12S is asymmetrical. This provides better coverage and provides the possibility of placing the electrodes 20S at more discrete locations around a blood vessel while still being able to compactly roll up the electrode structure 12S for insertion and retrieval. A plurality of electrodes 20S are provided on electrode structure 12S. Providing a plurality of electrodes 20S on each electrode structure allows selection of an electrode or a combination of electrodes to provide the most effective stimulation of a target nerve.

FIGS. 23A-23E show how an example electrode structure 12T may be rolled up and retracted into a tubular member 24T. In FIGS. 23A-E, pad 42T of electrode structure 12T is flexible enough that electrode structure 12T can be pulled into tubular member 24T by pulling shaft portion 14T (not visible) which is coupled to electrode structure 12T.

FIGS. 24A-24E show how an example electrode structure 12U may be rolled up, deployed, and retracted into a tubular member 24U. As shown in FIG. 24A, electrode structure 12U may initially be fully rolled up inside tubular member 24U (e.g., when nerve stimulation apparatus 10 is being inserted into a patient's blood vessel). The two halves of pad 42U of electrode structure 12U may be rolled up in the same direction.

As shown in FIGS. 24B and 24C, when nerve stimulation apparatus 10 is located in a desired position in the patient's blood vessel, electrode structure 12U may be deployed by moving electrode structure 12U out of tubular member 24U and opening pad 42U. As shown in FIGS. 24D and 24E, electrode structure 12U may be retrieved by turning or rotating shaft portion 14U from outside the body to roll up pad 42U. Once pad 42U is rolled up, electrode structure 12U can be retrieved into tubular member 24U. The entire tubular member 24U which contains electrode structure 12U can then be withdrawn from the patient's body.

Figure 25:
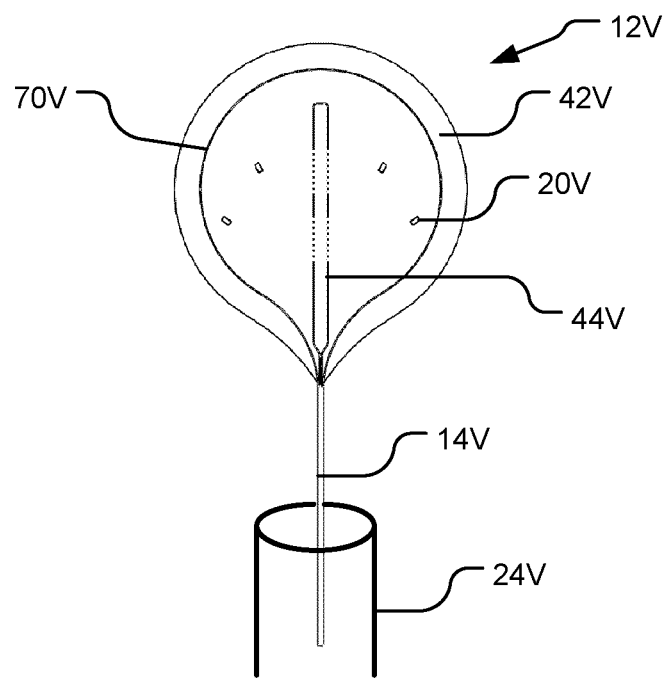
FIGS. 25 and 26 show two example electrode structures.
Figure 26:
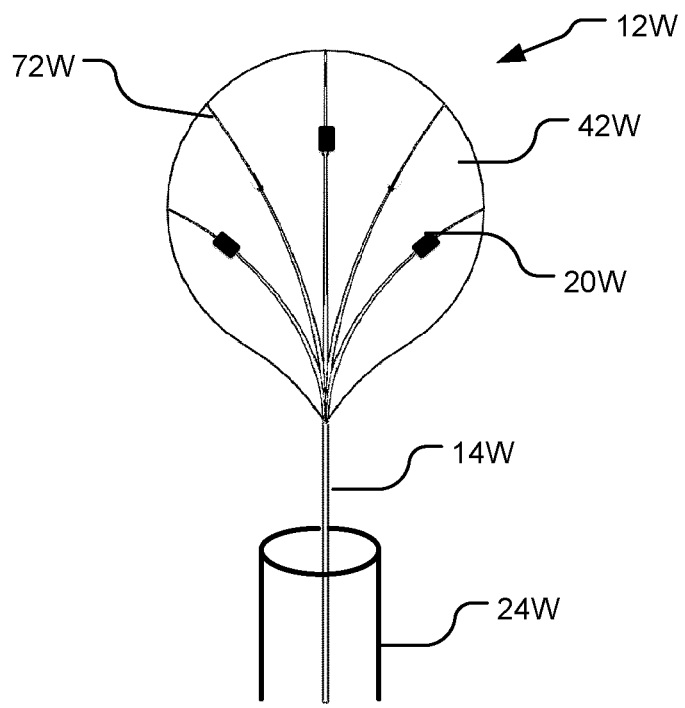

FIGS. 25 and 26 show two example electrode structures 12V, 12W. The FIG. 25 electrode structure 12V has a pad 42V that has a gentle curl (in cross section). Electrodes 20V are located on a convex side of pad 42V. Pad 42V comprises a low-stiffness spring wire loop 70V. In FIG. 25, wire loop 70V is in its relaxed, expanded configuration. Wire loop 70V may be made of nitinol or stainless steel, for example. Wire loop 70V may be located on the side of pad 42V that is facing the center of the blood vessel (e.g., the concave side of pad 42V) and opposite from the side where electrodes 20V are located. Alternatively, wire loop 70V may be sandwiched inside a pocket formed by two insulating pad layers of pad 42V. Electrodes 20V are exposed on the side of pad 42V that is facing the wall of the blood vessel (e.g., the convex side of pad 42V). Wire 44V is woven and adhered to pad 42V to provide structural support and stiffness to pad 42V. Electrode structure 12V may be withdrawn into tubular member 24V by pulling on shaft portion 14V from outside the body. On reaching the edge of tubular member 24V, the low stiffness deformable spring wire loop 70V collapses and pad 42V enters tubular member 24V. The tubular member 24V together with electrode structure 12V is then withdrawn from the body.

The FIG. 26 electrode structure 12W is similar to the FIG. 25 electrode structure 12V except that wire loop 70V is replaced with deformable low-stiffness springy ribs 72W. Electrode structure 12W may be retrieved into tubular member 24 in a similar fashion as electrode structure 12V.

Figure 27A:
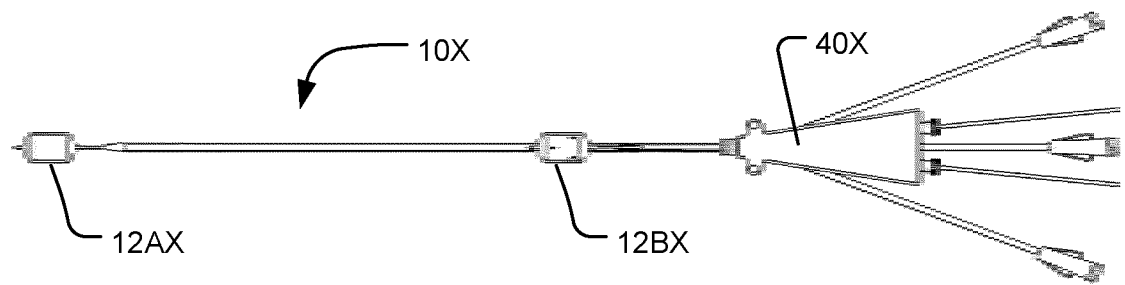
FIGS. 27A-27E schematically illustrate a nerve stimulation apparatus according to another embodiment.
Figure 27B:
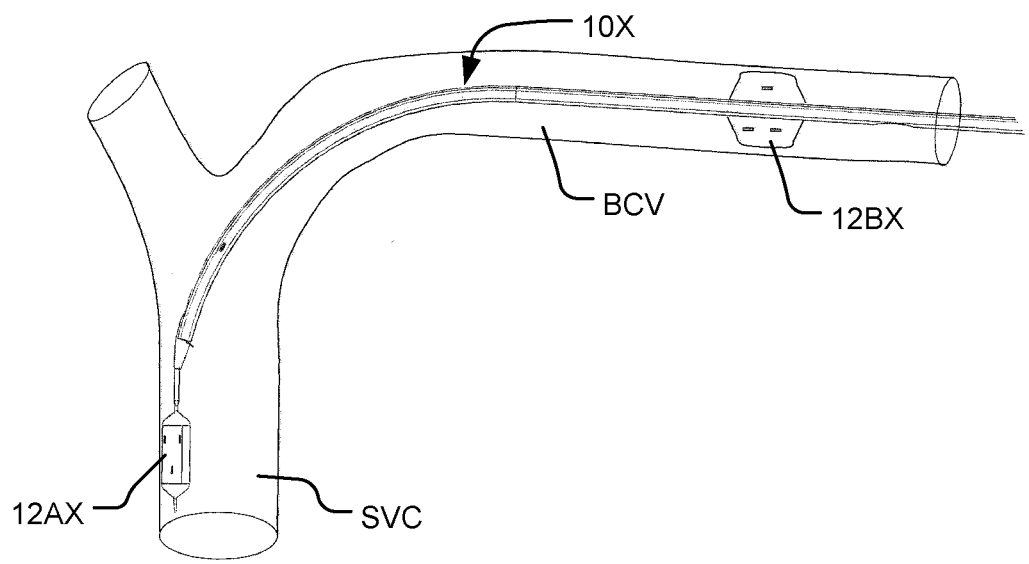
Figure 27C:
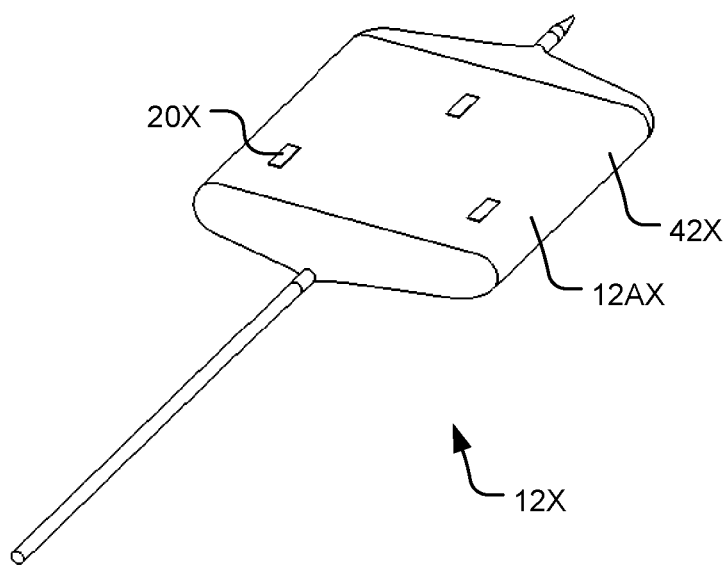
Figure 27D:
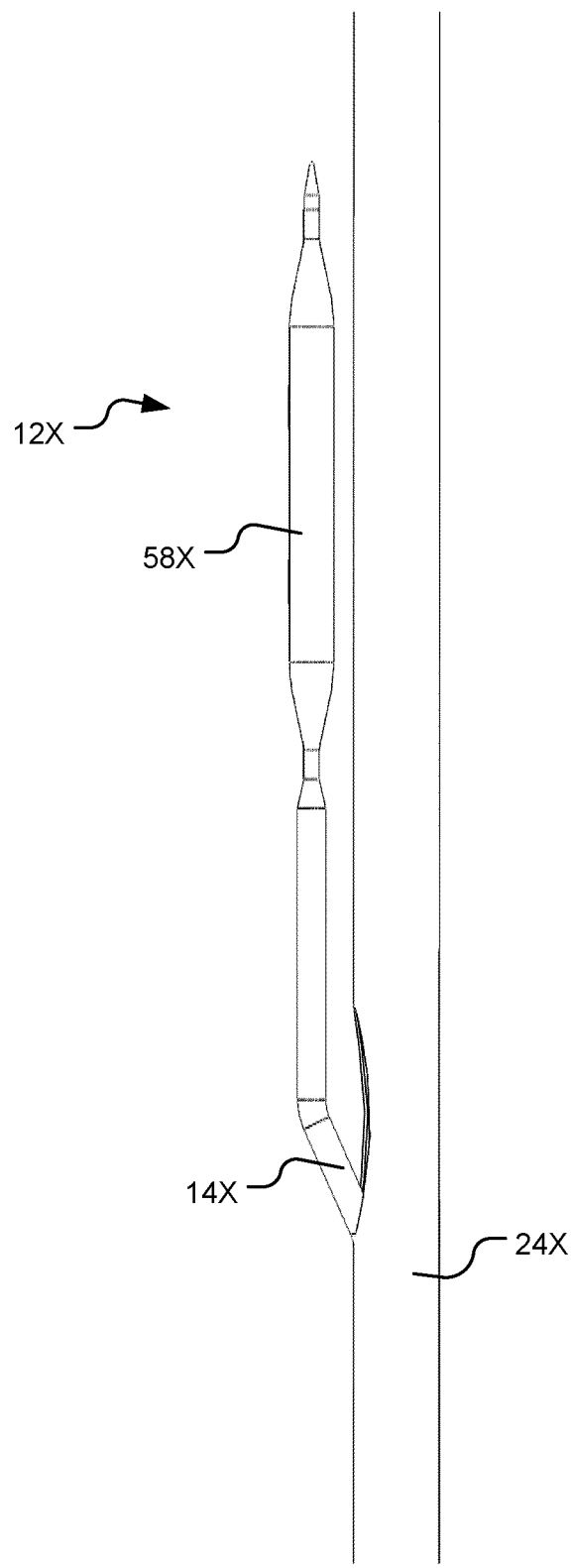
Figure 27E:
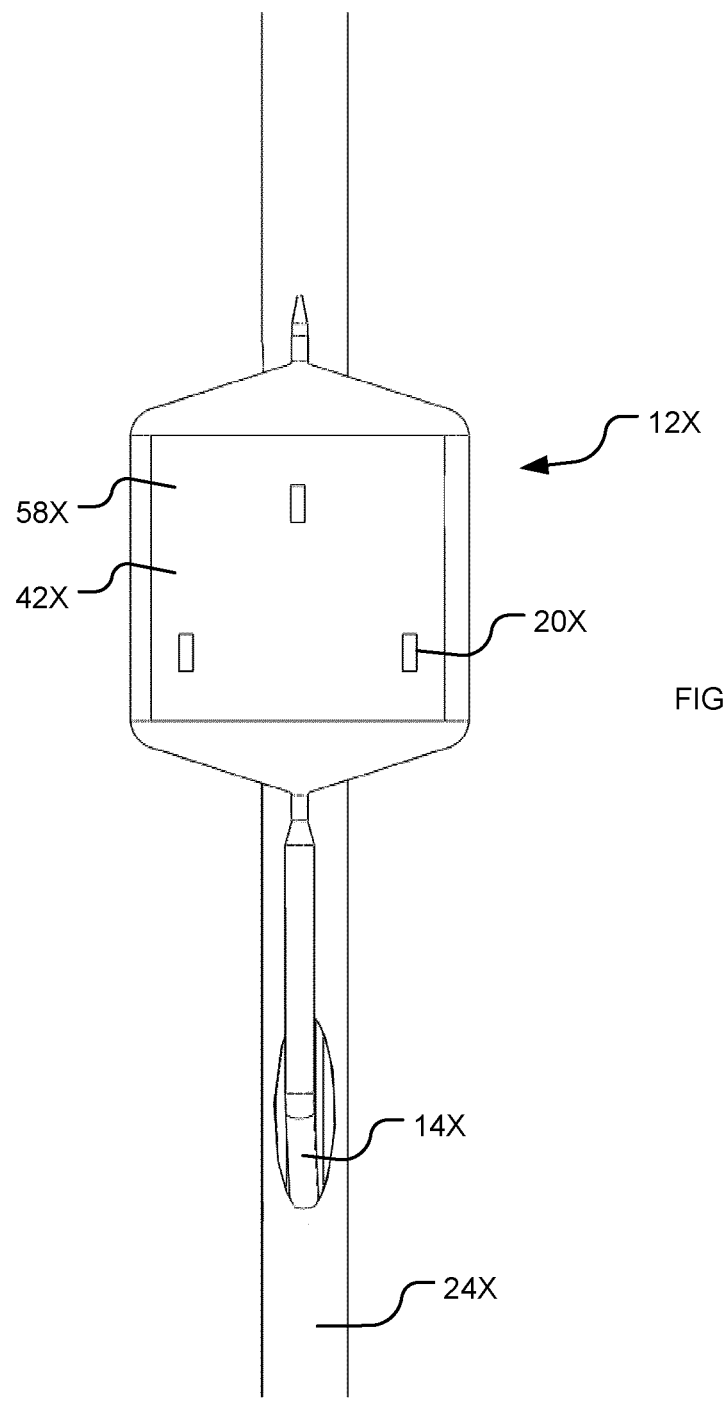

FIGS. 27A-27E schematically illustrate a nerve stimulation apparatus 10X according to another embodiment. FIG. 27A shows apparatus 10X coupled to a hub 40X. FIG. 27B shows apparatus 10X in position inside left BCV and SVC. Apparatus 10X comprises electrode structures 12AX, 12BX (collectively 12X). Electrode structures 12AX, 12BX may be the same or can be of different sizes and/or shapes. As shown in FIG. 27C, pad 42X of each electrode structure 12X comprises an inflatable balloon 58X. The inflatable balloon 58X may be made of a suitable polymer material (e.g., PET, nylon, silicone). The balloon 58X may be compliant, semi-compliant, or non-compliant. The balloon 58X may be inflated with a fluid (e.g, saline solution) and, once inflated, will take the desired shape. Electrodes 20X are disposed on one side of pad 42X. Electrodes 20X may be printed or glued on balloon 58X. Apparatus 10X also comprises a conduit for infusing fluid into balloon 58X, and the infusion of fluid into balloon 58X can be controlled from outside the body. FIG. 27D shows electrode structure 12X with balloon 58X in a deflated state. FIG. 27E shows electrode structure 12X with balloon 58X in a inflated state. Out of the package, balloon 58X is pleated and folded to wrap around shaft portion 14X. Balloon 58X is parked inside one of the lumens of apparatus 10X. To deploy electrode structure 12X, shaft portion 14X is pushed from the proximal end of apparatus 10X; balloon 58X pops out of an opening of tubular member 24X and then is inflated. To retrieve balloon 58X, balloon 58X is first deflated and then pulled into one of the lumens of apparatus 10X from the proximal end of apparatus 10X via shaft portion 14X.

Figure 28A:
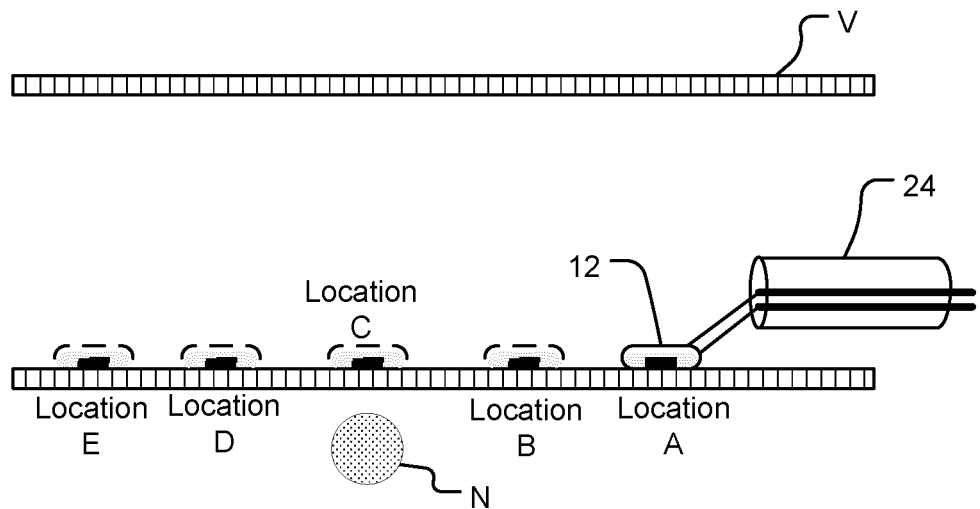
FIGS. 28A, 28B show an example method for locating an electrode structure in a blood vessel V to stimulate a target nerve.
Figure 28B:
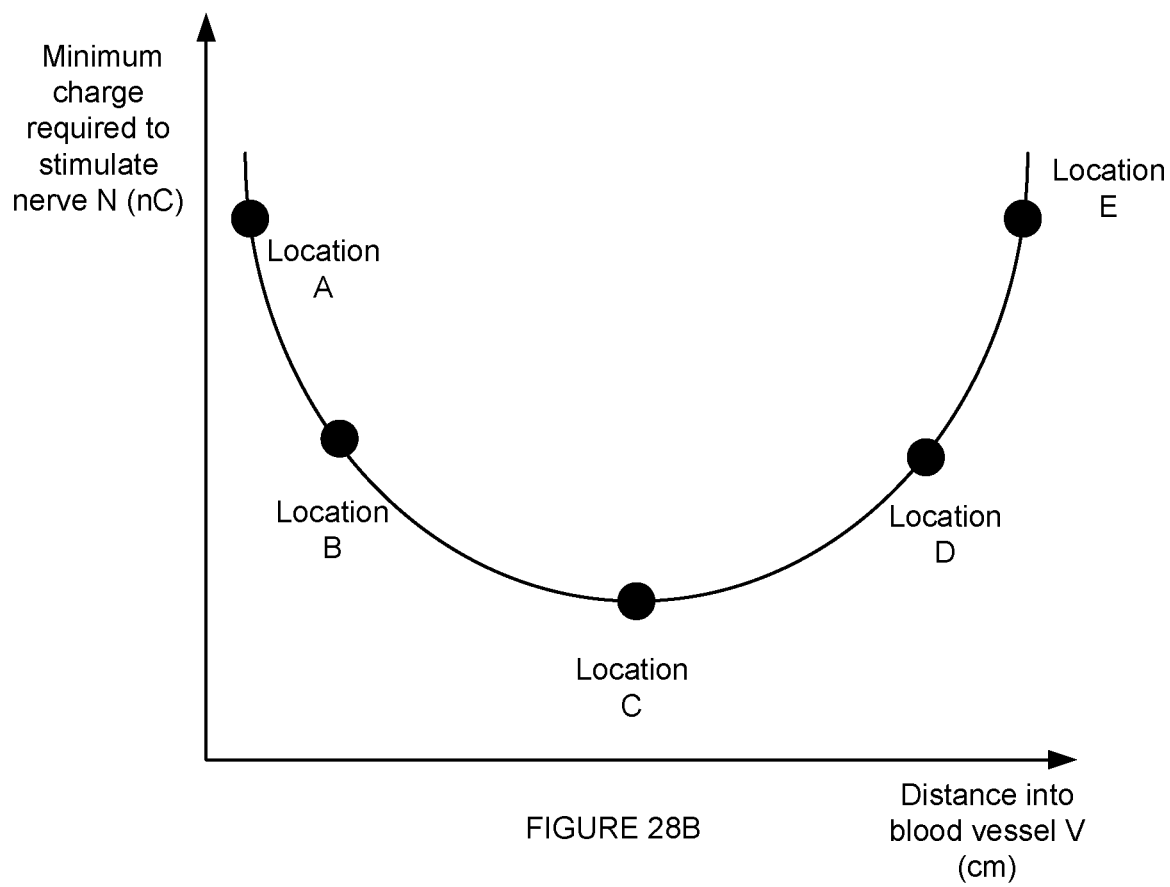

FIGS. 28A, 28B show an example method for locating electrode structure 12 in a blood vessel V to a target nerve N. In this method, electrode structure 12 is inserted into blood vessel V while electrode structure 12 is retracted within tubular member 24. Electrode structure 12 is then extended out of tubular member 24 and positioned at location A. At this point, the amount of electric current required to stimulate nerve N is measured using a suitable device. This may be done, for example, by detecting muscle activity as a result of nerve stimulation, for example, diaphragm muscle activity as result of phrenic nerve stimulation. Electrode structure 12 is then retracted into tubular member 24. Then tubular member 24 is advanced in blood vessel V for a small distance (e.g., 0.1 mm, 0.2 mm, 0.5 mm, 1 mm, 2 mm, 5 mm, etc.) and electrode structure 12 is then extended out of tubular member 24 and positioned at Location B. Again, the amount of electric current required to stimulate nerve N is measured using a suitable device. These steps are repeated (e.g. at Location C, Location D, Location E) for as many times as necessary.

By making a set of such measurements, one can obtain a function indicating how the amount of electric current required to stimulate nerve N varies in relation to the position of electrode structure 12 along blood vessel V. FIG. 28B shows a schematic graph of such a function. In this graph, the amount of electric current required to stimulate nerve N is the lowest at Location C. Therefore, in this illustration, Location C is a desirable or optimal location to place electrode structure 12 as compared to Locations A, B, D and E. This method can be practised either manually or in conjunction with a suitable machine, such as a graphing calculator or a computer.

One aspect of the invention relates to sensors for sensing and/or monitoring the position of an electrode structure 12 inserted into a blood vessel and associated methods. The sensor may be optionally disposable. The sensor may be placed outside of the patient's body. The sensor may be fixed to the reference frame of the patient's body. As an electrode structure 12 is advanced and/or rotated in a blood vessel by a therapist, the sensor acquires positional data and can also relay data to a control unit where electrode position is monitored simultaneously with stimulation parameters and results of stimulation. The control unit calculates the best placement of electrodes 20 and can store this information or provide feedback to the therapist in real time or at later times.

A nerve stimulation system according to an embodiment of the present invention may comprise the following: an intravascular nerve stimulation apparatus having flexible tubular member(s) that can be inserted, advanced, and/or rotated in a blood vessel; one or more sensors that track the position of the intravascular electrodes; and a control unit that acquires position data and relays it to the therapist and/or stores it for later use. Typically, the sensor is coupled to a proximal part of a shaft portion of the nerve stimulation apparatus. The sensor may be placed outside of the body.

FIG. 29A schematically shows an example embodiment of a sensor 80A that is independent from an introducer or tubular member of an intravascular nerve stimulation apparatus 10. FIG. 29B schematically shows an example embodiment of a sensor 80B that is integrated with an introducer or tubular member of an intravascular nerve stimulation apparatus 10.

In some embodiments, the sensor is a pressure-sensitive variable resistance potentiometer sensor. Such a sensor is suitable for monitoring the position (depth) of an intravascular electrode inside a blood vessel. The sensor supplies a voltage output signal that is approximately linearly proportional to the position of the electrode. FIGS. 29C and 29D show an example sensor 80C in cross-sectional and perspective views. Sensor 80C comprises a pressure-sensitive linear potentiometer 81. A low-friction bead 82C (e.g., a Teflon bead) is fixed onto an elongate shaft portion 14. Potentiometer 81, bead 82, and part of shaft portion 14 are assembled within a guide chamber 84C to form sensor 80C. Sensor 80C may be fixed either to the patient, or to the tubular member or the introducer of a nerve stimulation apparatus. As the shaft portion 14 advances, the bead 82 slides along and exerts pressure on potentiometer 81, therefore changing its resistance. The point of contact of the bead 82 against the potentiometer 81 provides a signal that, provided that the shaft portion 14 does not buckle, is generally linearly proportional to the intravascular position of the electrode 20.

Figure 29F:
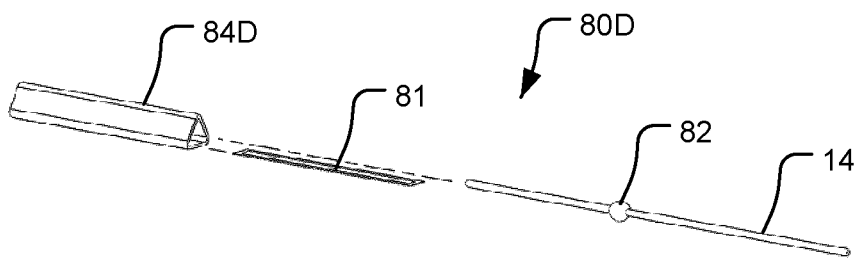
FIGS. 29A to 30H shows various sensors which may be used with the nerve stimulation apparatus described herein as well as in other contexts.
Figure 29G:
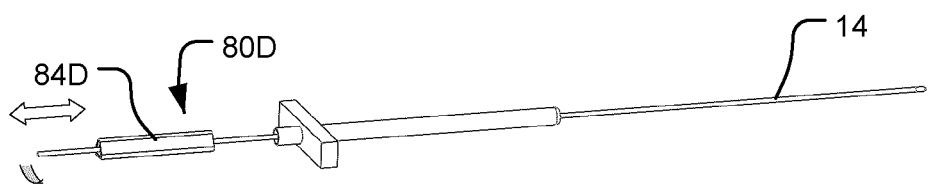
Figure 29H:
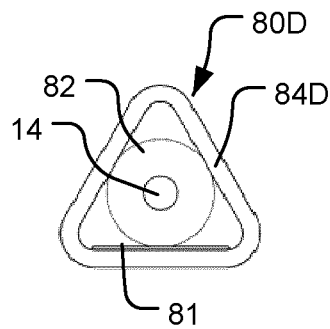

The length of the active region of the potentiometer 81 limits the distance over which the depth of the electrode 20 can be tracked. In some embodiments, a commercially available flexible potentiometer may be used with a 6 cm long active region which is sufficient to monitor the movement of an electrode in the vicinity of its target phrenic nerve. However, potentiometers of any desired length may be manufactured for this purpose. If shaft portion 14 has a circular cross-section and bead 82 is spherical and coaxial the shaft portion 14, the shaft portion 14 can be rotated while maintaining contact with the potentiometer 81 to obtain the angular positions of the shaft portion 14 and electrode 20. FIGS. 29F-H show an additional example embodiments of sensor 80D, wherein the guide chamber 84D has a generally triangular cross-section.

Figure 29L:
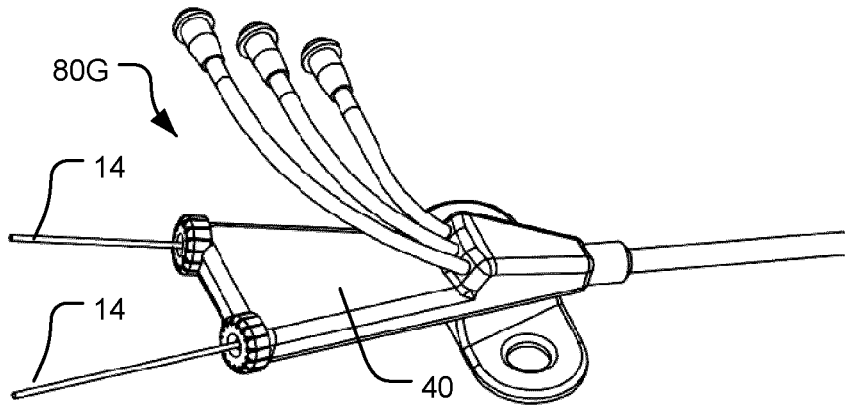

In some embodiments, sensor 80 is integrated with the hub of a nerve stimulation apparatus. An example sensors 80G is shown in FIG. 29L. The depth and the angular position of an intravascular electrode can be monitored by combining the use of a linear potentiometer as described above, plus a circular potentiometer to monitor rotation of the shaft portion. Alternatively, the angular position can be controlled by a series of "click stops" placed at convenient angles (e.g., one stop every 15° or 30°) over a desired angular range (e.g., +/−90° from a central default angular position of an electrode) and a multi-pole electrical switch can be connected to indicate each click stop. To monitor rotation of the shaft portion, the shaft portion proximal to the linear transducer can be modified to be of non-circular cross-section, for example square cross-section, and a dial can be incorporated with a square hole through which the shaft portion travels. The therapist can manually rotate either the shaft portion itself or its associated dial, and the rotational movement of the dial is sensed by an integrated sensor housed inside the hub of the nerve stimulation apparatus or alternatively by a multi-pole electrical switch with pre-set click stops. FIG. 29L shows an embodiment wherein the shaft portions 14 can be rotated by dials.

Figure 29M:
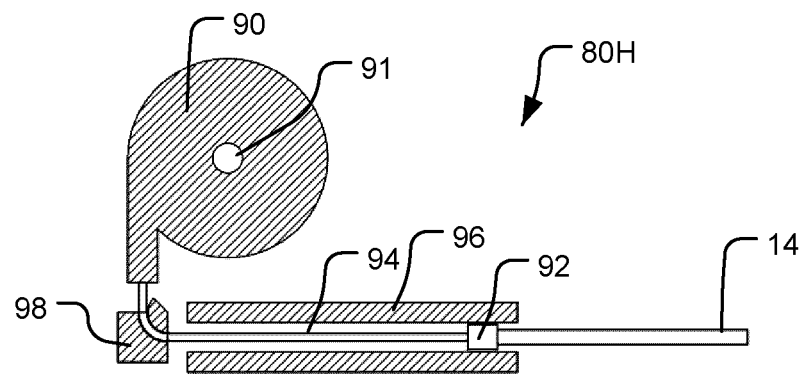

FIG. 29M shows an embodiment of a sensor 80H in which the shaft portion 14 is coupled by way of a string or other flexible element to a spring-loaded shaft fitted with a rotational sensor 90. The rotational sensor's rotational axis 91 is fitted with a rotational encoder (not shown in FIG. 29M), which can be converted into a linear displacement measurement. The shaft portion 14 is attached to rotational sensor 90 using a collar 92 and a wire 94. As the shaft portion 14 is moved, the collar 92 slides through a guide 96 which prevents the shaft portion 14 from moving in any axis other than the one in which the rotational sensor 90 keeps track of position. To make the assembly smaller, rotational sensor 90 may be put at an angle by having the wire 94 redirected by a pulley or a block 98. To move the shaft portion 14, the collar 92 can be fitted with a slider or the assembly can allow the user to move the shaft portion 14 directly.

Figure 29N:
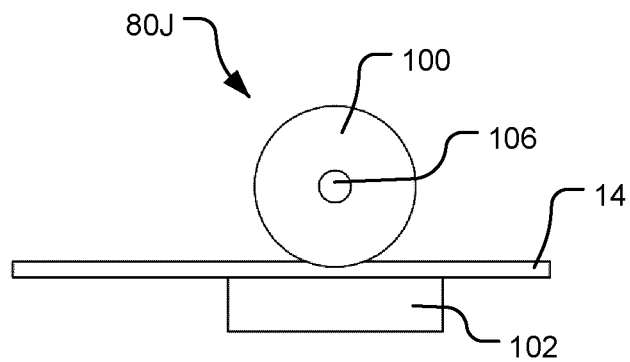
Figure 29O:
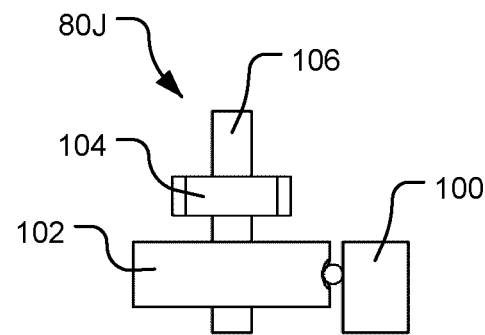

FIGS. 29N and 29O are side and front views of a sensor 80J where the shaft portion 14 is fitted between a roller 100 and a guide 102. As the shaft portion 14 passes the roller 100, it creates a rotational motion of the roller 100 in the same direction. The rotational movement of the roller 100 is then converted to a linear movement through an encoder 104. Both roller 102 and encoder 104 are located co-axially on a rotational axis 106.

Figure 29P:
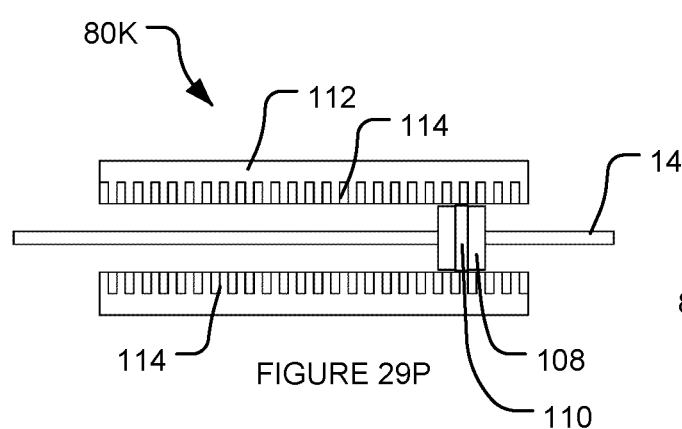

FIG. 29P shows a sensor 80K wherein shaft portion 14 is fitted with a collar 108 made out of an insulating material. The collar 108 has at least one conductive ring 110. Ring 110 slides through a guide 112 fitted with electrical contacts 114. As the collar 108 slides through the guide 112 and the ring 110 touches the electrical contacts 114 on each side, a current passes through the ring 110. The current may be converted to positional data, either by correlating position to resistance or by identifying the shorted contacts and associating them with a calibrated position.

Figure 29Q:
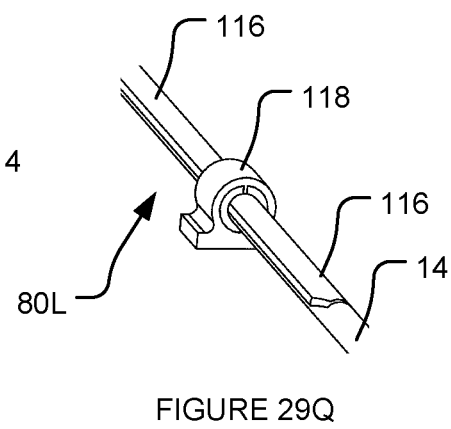

FIG. 29Q shows a sensor 80L in which a shaft portion 14 is fitted with two resistive traces 116 connected at one end. Both resistive traces 116 are exposed, but the bridge connecting them is not. As the shaft portion 14 slides into ring guide 118, both traces 116 contact two halves of a metallic ring. A current is sent through one half, and received via the other half. The current goes through the traces 116 on the shaft portion 14. The voltage drop measured across the ring halves is proportional to the length of the traces 116 the current goes through. By calibrating the resistance, a position measurement can be obtained.

One or more angle sensors may be used with the apparatus described herein. FIG. 30A shows an example angle sensor 200 (in side view) in which a lead with a non-circular profile slides through a disc which is free to rotate. Angle sensor 200 comprises wiper 202 (FIG. 30B) and potentiometer 204

(FIG. 30C). When the lead is rotated, the sleeve rotates with the wiper 202 that applies a pressure on cylindrical membrane potentiometer 204.

Figure 30D:
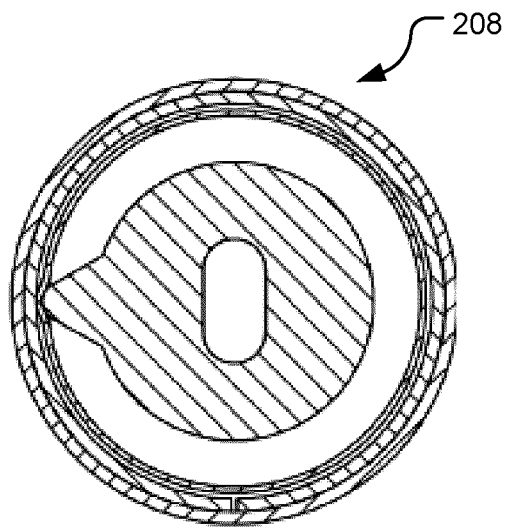
Figure 30E:
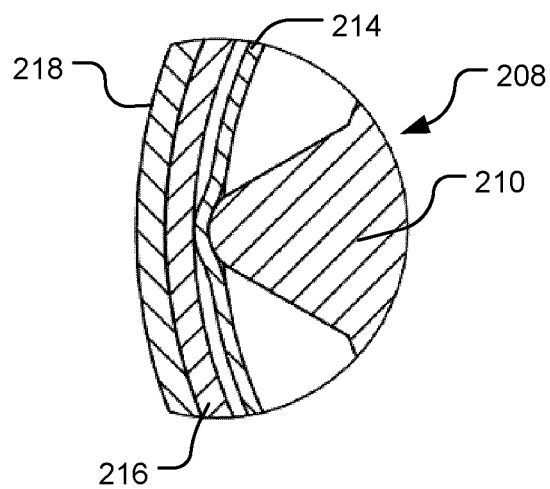
Figure 30F:
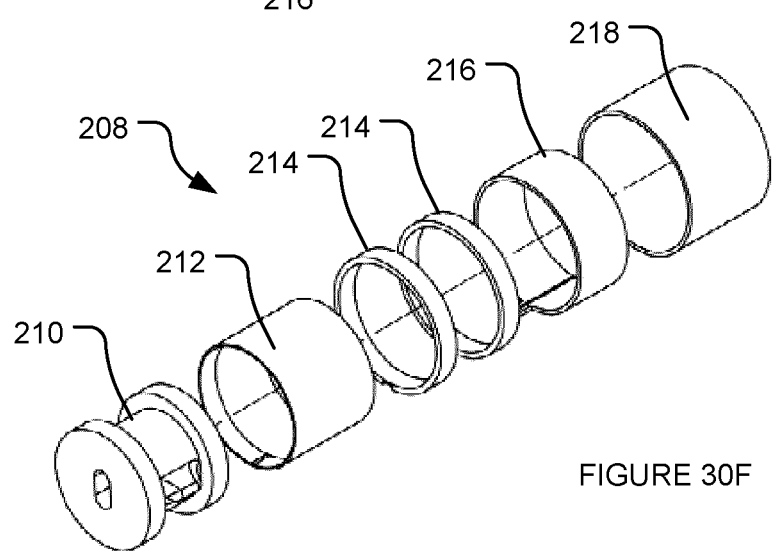

FIGS. 30D to 30F shows an example angle sensor 208 in which a lead with a non-circular profile slides through a sleeve 210 which is free to rotate. FIG. 30D is a cross-sectional view of sensor 208. FIG. 30E is a side view of sensor 208. FIG. 30F is an exploded view of sensor 208. When the lead is rotated, the sleeve 210 rotates with a wiper part 211 that applies a pressure on a potentiometer. Sensor 208 comprises sleeve 210 with wiper 211, conductive membrane 212, space layers 214, resistive trace 216 and support structure 218.

Figure 30G:
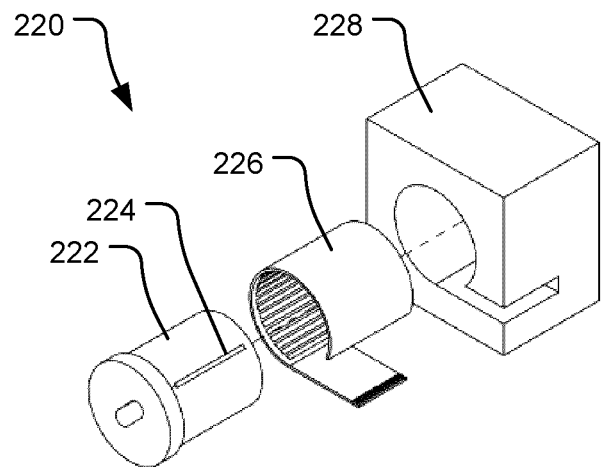
Figure 30H:
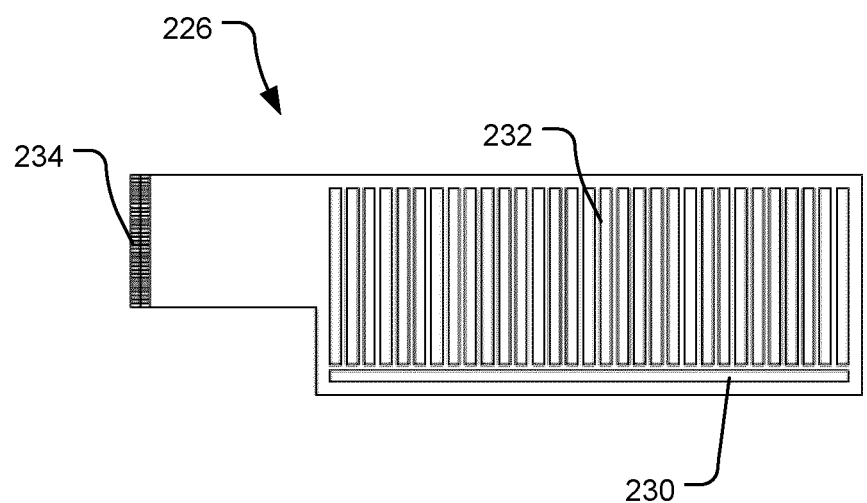

FIGS. 30G and 30H show an angle sensor 220 in which a lead with non-circular profile slides through a sleeve which is free to rotate. Sensor 220 comprises sleeve 222 having a conductive strip 224, a flexible PCB 226, and a support structure 228. The flexible PCB 226 comprises electrical contacts 234, measurement traces 232, and a perpendicular trace 230. When the lead is rotated, the sleeve 222 rotates and creates an electrical contact with a cylindrical board with multiple contacts. This part may be a flexible PCB 226 with a series of parallel exposed traces 232 and one perpendicular trace 230. The perpendicular trace is then energized and shorted with one of the other traces via a conductive strip on the rotating sleeve. A control unit then cycles through the contacts and looks for the traces that are energized to find the position. The conductive part shorting the traces can be shorting only the energized trace with another, or more than one. For example, the conductive part could short all traces but one, so that the control unit would look for the trace that is not energized.

Figure 31A:
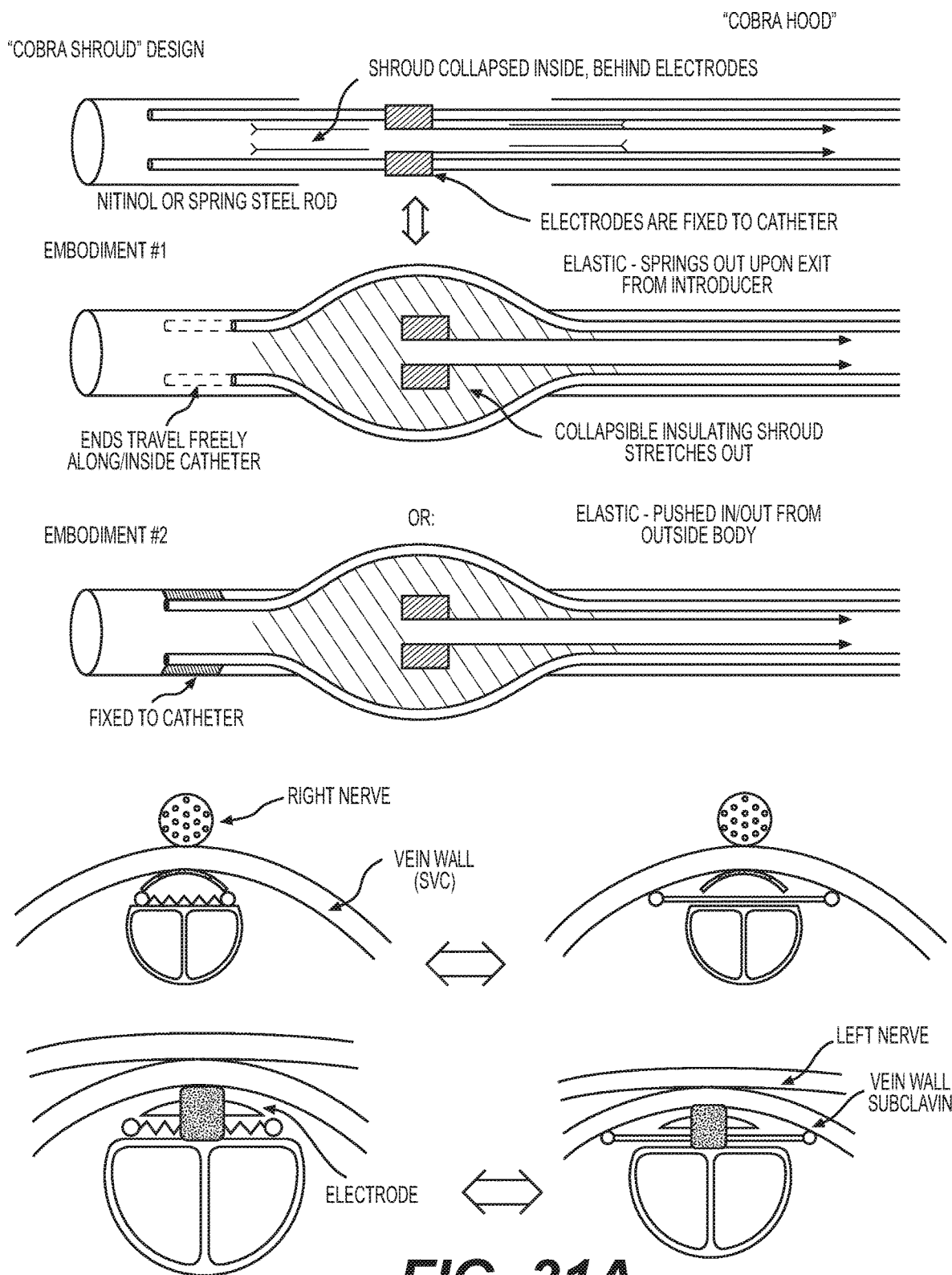
FIGS. 31A to 31E shows an example shroud design which may be used with the nerve stimulation apparatus described herein as well as in other contexts.
Figure 31B:
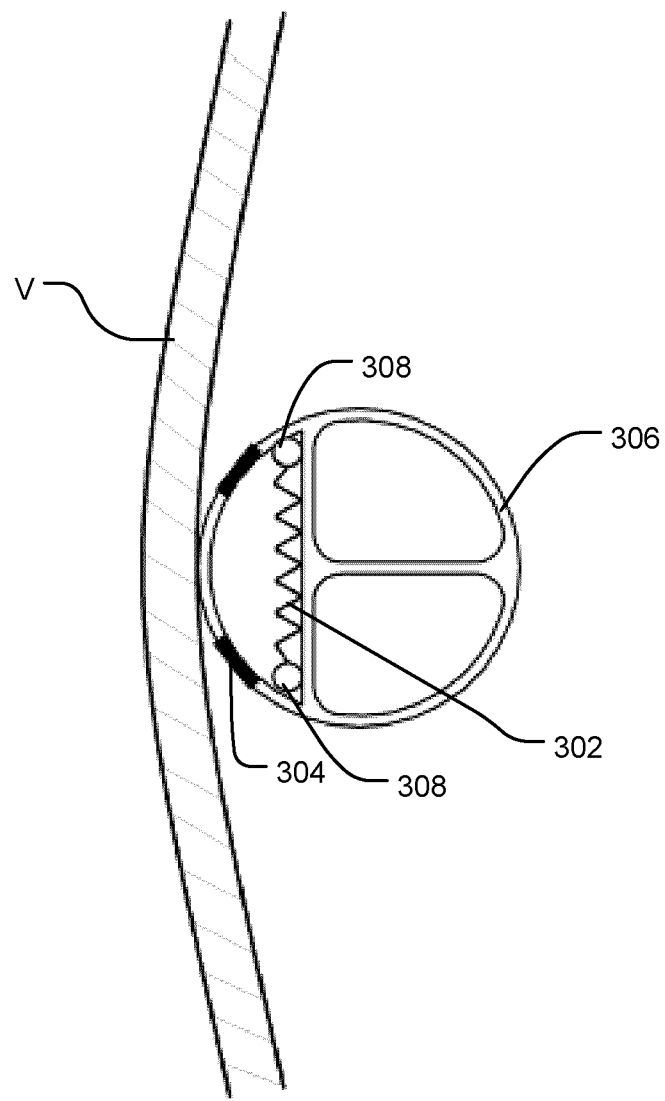
Figure 31C:
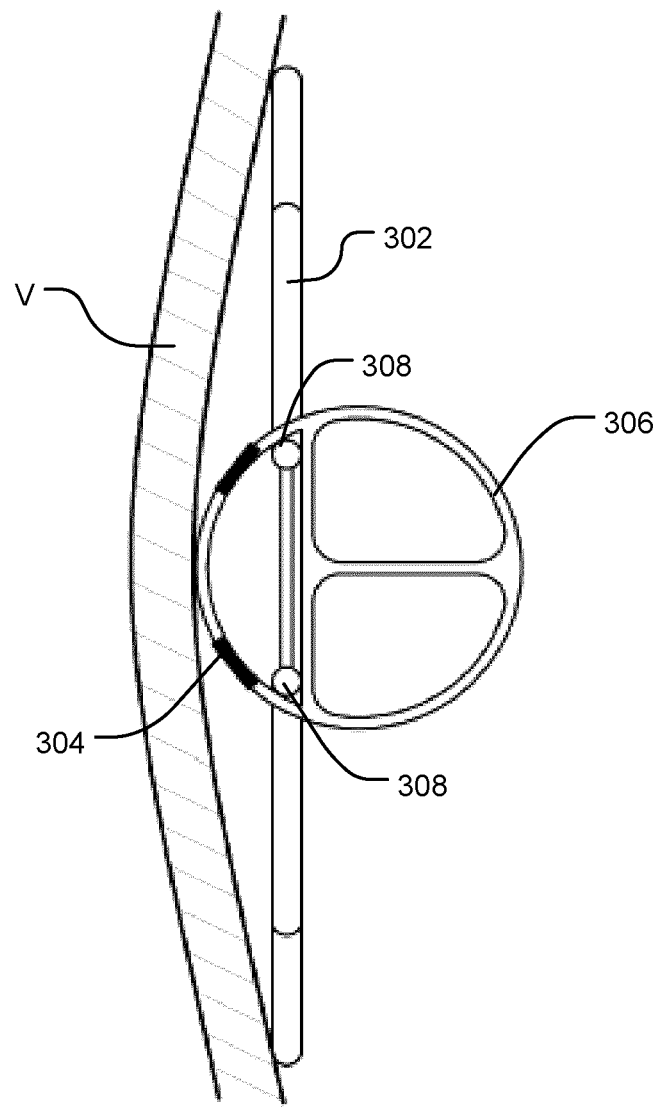
Figure 31D:
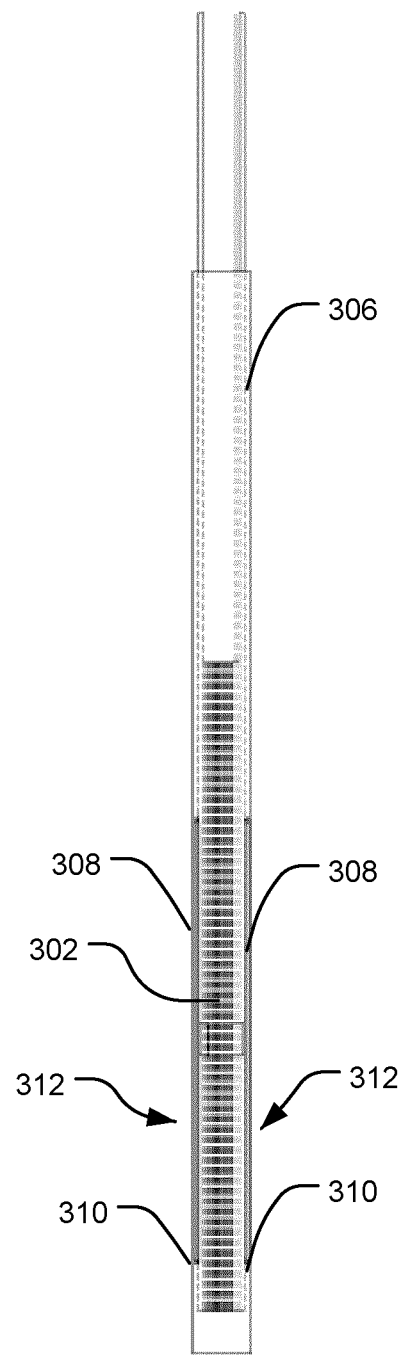
Figure 31E:
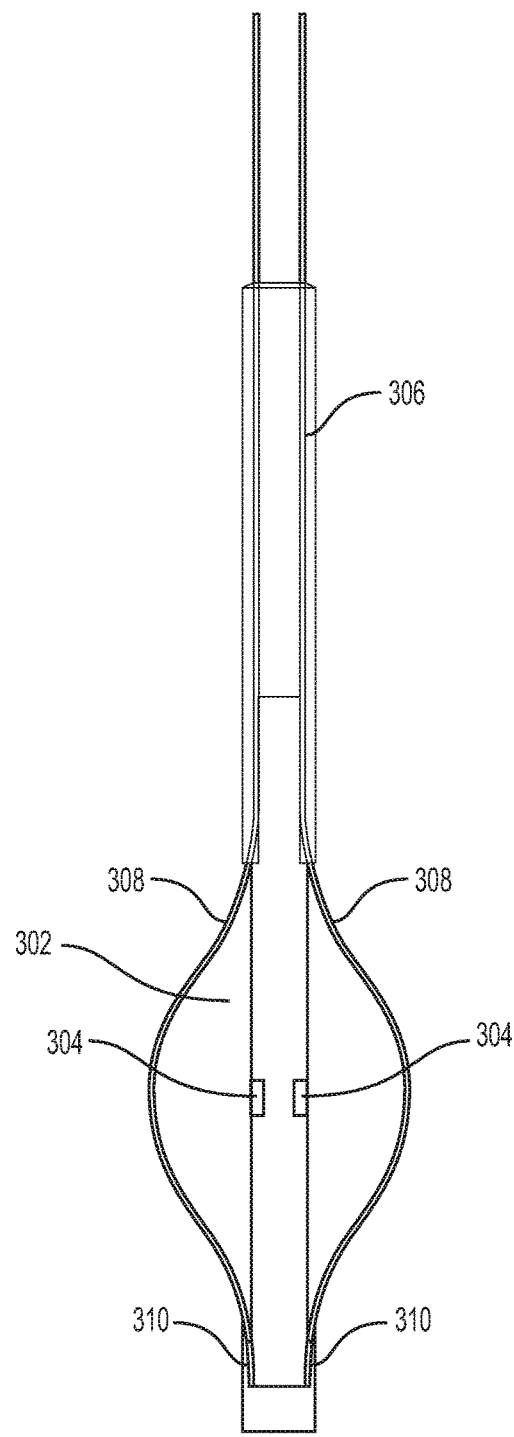

FIGS. 31A-31D show a "cobra hood" expandable design which may be used in combination with the electrode structure of the nerve stimulating apparatus described herein as well as in other contexts. Such a design may be used, for example, to provide a backing member (e.g., petal) for one or more electrodes. For example, such a structure may be deployed to stimulate the left phrenic nerve. FIG. 31B is a schematic cross-sectional view of the cobra design wherein an expandable shroud 302 is in an unexpanded configuration. FIG. 31C is a schematic cross-sectional view of the cobra design wherein shroud 302 is in an expanded configuration. FIG. 31D is a schematic plan view of the cobra design wherein shroud 302 is in an unexpanded configuration. FIG. 31E is a schematic plan view of the cobra design wherein shroud 302 is in an expanded configuration. unexpanded configuration. One or more electrodes 304 may be located above or on top of shroud 302, oriented towards an inner surface of a blood vessel V.

Shroud 302 may be connected to and/or supported by a pair of flexible members such as rods or tubes 308 which run inside tubular member 306 when shroud 302 is not deployed. The flexible members may be resiliently flexible. Rods or tubes 308 may be made of stainless steel, Nitinol, or some other suitable material, for example. The distal ends of rods or tubes 308 may be anchored or fixed to tubular member 306 at anchor positions 310. In alternative embodiments, distal ends of rods or tubes 308 may move freely to some extent along the tubular member 306. Tubular member 306 comprises side openings 312.

Shroud 302 can be manipulated from outside the body to move between a collapsed configuration and an expanded configuration. When a user pushes the proximal ends of rods or tubes 308 towards the distal ends, portions of rods or tubes 308 along side openings 312 bulge out and extend out of side openings 312 of tubular member 306. This in turn stretches shroud 302 to open to an expanded configuration. When shroud 302 is expanded, it forms a petal-like backing member for electrodes 304. Shroud 304 may help to position electrodes 304 against the blood vessel wall. The electrically insulating shroud also functions as an electrically insulating backing sheet which helps to insulate electrodes 304 from the blood flowing in the lumen of the blood vessel.

To return shroud 302 into tubular member 306, the force applied to rods or tubes 308 is released. Rods or tubes 308 are returned to a straight configuration and retrieved into tubular member 306. This in turn brings shroud 302 into a collapsed configuration inside tubular member 306.

The "cobra" design shown in FIGS. 31A-31E may be altered to produce a "half cobra" design. In a "half cobra" design, one edge of shroud 302 is connected to and/or supported by a rod or tube 308; the other edge of shroud 302 is fixed inside tubular member 306 (e.g., fixed to an inside surface of tubular member 306). When rod or tube 308 is manipulated to bulge out, shroud 302 expands to one side to form a "half cobra" backing sheet in an expanded configuration. A device may comprise two "half cobra" shrouds side by side which together form a "full-cobra" backing sheet in operation.

Electrodes 304 could be located on tubular member 306. Instead of or in addition to electrodes 304 on tubular member 306, electrodes 304 could be on shroud 302. Where flexible members 308 are electrically conductive, portions of flexible member 308 may be exposed to provide electrodes.

The applications of the apparatus and methods described herein are not limited to phrenic nerves. The apparatus and methods described herein may be applied to provide surgically simple, low risk solutions for stimulating a wide range of peripheral or cranial nerves. For example, the methods and apparatus may be applied to stimulate the obturator nerve in the hip/groin area or the trigeminal nerve in the head.

The apparatus and methods may be applied to treatment of a wide variety of disorders such as pain of peripheral or craniofacial origin, sensory deficits, paralysis or paresis of central origin, autonomic disorders, and generally any medical condition that can be treated or alleviated using neuromodulation by electrical stimulation of a nerve that is in close proximity to a blood vessel into which a nerve stimulation apparatus can be deployed.

Various elements of the invention may be used alone, in combination, or in a variety of arrangements not specifically discussed in the embodiments described in the foregoing. For example, elements described in one embodiment may be combined with elements described in other embodiments to yield further example embodiments.

The scope of the invention should not be limited by the embodiments set forth in the examples, but should be given the broadest interpretation consistent with the description as a whole.

What is claimed is:

1. An intravascular electrode system comprising: a resiliently-flexible support member;
   a plurality of electrodes supported at spaced-apart locations on the resiliently-flexible support member, wherein the support member has a plurality of lumens and is bendable to follow a path of a curved blood vessel, and wherein restoring forces resulting from the resilience of the support member are adapted to hold one or more of the plurality of electrodes in place against a wall of the blood vessel;
   wherein the support member has an initial radius of curvature to which it tends to return, wherein the initial radius of curvature is adapted to be greater than that of a radius of curvature of the blood vessel, the blood vessel comprising a human left brachiocephalic vein and superior vena cava.

2. A system according to claim 1 wherein the plurality of electrodes comprise a first plurality of electrodes and a second plurality of electrodes spaced apart along the support member by a distance selected to allow the first and second pluralities of electrodes to be adapted to be respectively located proximate to first and second nerves passing nearby the blood vessel.

3. A system according to claim 2 comprising a stimulation device connected to selectively apply electric current to electrodes of the first plurality of electrodes, the second pluralities of electrodes, or both the first and second pluralities of electrodes, the electric current adapted to be selected to stimulate the first nerve, the second nerve, or both the first and second nerves, respectively, to cause a diaphragm muscle of a patient to contract to cause inhalation of air into the patient's lungs.

4. A system according to claim 2 comprising a control unit adapted to select which electrodes of the first plurality of electrodes most effectively stimulate the first nerve and which electrodes of the second plurality of electrodes most effectively stimulate the second nerve.

5. A system according to claim 4 wherein the control unit is connected to acquire position data from a position measurement device, to one or both: relay the position data to a user and store the position data, and monitor stimulation parameters and results of stimulation simultaneously with the position data.

6. A system for treating a patient, the system comprising:
the intravascular electrode system of claim 2, wherein:
the support member comprises a tubular catheter configured for insertion into the blood vessel, the catheter defining the plurality of lumens extending from a proximal end of the catheter towards a distal end of the catheter;
the first nerve comprising a right phrenic nerve and the second nerve comprising a left phrenic nerve;
the first plurality of electrodes are proximate the distal end of the catheter and oriented for selectively stimulating the right phrenic nerve; and
the second plurality of electrodes are coupled to the catheter proximal to the first set of electrodes and oriented for stimulating the left phrenic nerve; wherein each of the first and second pluralities of electrodes comprises multiple pairs of electrodes, wherein at least one pair of electrodes of each of the first and second pluralities of electrodes have different circumferential orientations with respect to a longitudinal centerline of the catheter; and
one or more leads comprising:
a first plurality of electrical leads extending through at least one lumen of the plurality of lumens from the proximal end of the catheter to the first plurality of electrodes; and
a second plurality of electrical leads extending through at least one lumen of the plurality of lumens from the proximal end to the second plurality of electrodes.

7. A system according to claim 6 wherein at least one of the plurality of lumens is in fluid communication with a proximal opening and a corresponding distal opening in the catheter.

8. A system according to claim 6 wherein at least one of the plurality of lumens is configured for at least one of removing blood samples, inserting medication into the blood vessel, delivering nutrients or other fluid into the blood vessel, or measuring a parameter of blood.

9. A system according to claim 2 wherein the first and second pluralities of electrodes are separated by a distance in the range of 5 cm to 10 cm, the first and second plurality of electrodes are oriented at a 90 degree angle to one another, or both.

10. A system according to claim 2 wherein the plurality of electrodes are supported on a convex surface of an insulating backing member, the backing member being movable between an expanded configuration and a folded configuration wherein:
when the backing member is in the folded configuration, the electrodes can be retrieved inside a delivery tube; and
when the electrode structure is outside of the delivery tube, the backing member is movable to the expanded configuration.

11. A system according to claim 10 wherein the first plurality of electrodes are supported on one backing member and the second plurality of electrodes are supported on another backing member.

12. A system according to claim 10 wherein the backing member comprises one of a sheet capable of unrolling, a pad or hood capable of expanding and collapsing, a wire loop, or an inflatable balloon.

13. A system according to claim 1 wherein the plurality of electrodes are electrically coupled to one or more leads in a one-to-one relationship, and each of the two or more electrodes is individually addressable.

14. A system according to claim 1 wherein the support member is more flexible in one direction than in another.

15. A system according to claim 1 wherein a distal portion of the support member is more flexible than a proximal portion of the support member.

16. A system according to claim 1 comprising a sensor for monitoring at least one of temperature, oxygen levels, CO2 levels, bioelectrical activity, or electrode position.

17. A system according to claim 1 comprising a position measurement device configured to one or both: measure a longitudinal displacement of the support member along the blood vessel and monitor an angle of rotation of the support member.

18. A system according to claim 1 comprising one or more electrodes for ECG monitoring.

19. The intravascular electrode system of claim 1, wherein at least one of the plurality of electrodes is printed on the support member.

20. An intravascular electrode system comprising: a resiliently-flexible support member;
a plurality of electrodes supported at spaced-apart locations on the resiliently-flexible support member, wherein resilience of the support member is adapted to permit a radius of curvature along a length of an outer surface of the support member to decrease as the support member follows a path of a curved blood vessel, and wherein restoring forces resulting from the resilience of the support member are adapted to hold one or more of the plurality of electrodes in place against a wall of the blood vessel;
a position measurement device configured to one or both: measure a longitudinal displacement of the support member along the blood vessel and monitor an angle of rotation of the support member; and
one or more leads within the support member.

21. The intravascular electrode system of claim 20, wherein the support member has a plurality of lumens.

22. The intravascular electrode system of claim 21, wherein at least one of the plurality of lumens is configured for at least one of removing blood, inserting medication into the blood vessel, delivering nutrients or other fluid into the blood vessel, or measuring a parameter of blood.

23. The intravascular electrode system of claim 21, wherein the outer surface of the support member has one or more openings, and at least one of the plurality of lumens is in fluid communication with an opening of the support member.

24. The intravascular electrode system of claim 20, wherein at least one of the plurality of electrodes is movable between a retracted position and a deployed position.

25. The intravascular electrode system of claim 20, wherein the support member is a catheter.

26. The intravascular electrode system of claim 20, further comprising a resilient shaft inside the support member.

27. The intravascular electrode system of claim 20, wherein at least one of the plurality of electrodes comprises a ribbon coupled to at least one of the one or more leads.

28. The intravascular electrode system of claim 20, wherein at least one of the plurality of electrodes is printed on the support member.

29. The intravascular electrode system of claim 20, wherein the plurality of electrodes comprise a first plurality of electrodes and a second plurality of electrodes spaced apart along the support member by a distance selected to allow the first and second pluralities of electrodes to be adapted to be respectively located proximate to first and second nerves passing nearby the blood vessel.

30. The intravascular electrode system of claim 29, wherein the first and second pluralities of electrodes are oriented at a 90 degree angle to one another.

31. The intravascular electrode system of claim 20, wherein the plurality of electrodes are electrically coupled to the one or more leads in a one-to-one relationship and each of the two or more electrodes is individually addressable.

32. The intravascular electrode system of claim 20, further comprising a stimulation device connected to selectively apply electric current to one or more of the plurality electrodes, the electric current adapted to be selected to one or more of the plurality electrodes to cause a diaphragm muscle of a patient to contract to cause inhalation of air into the patient's lungs.

33. The intravascular electrode system of claim 20, further comprising a control unit adapted to select which electrodes of the plurality of electrodes most effectively stimulate a nerve.

34. The intravascular electrode system of claim 20, wherein the plurality of electrodes comprise a first and a second pluralities of electrodes separated by a distance in the range of 5 cm to 10 cm.

35. The intravascular electrode system of claim 20, further comprising a sensor for monitoring at least one of temperature, oxygen levels, CO2 levels, bioelectrical activity, or electrode position.

36. The intravascular electrode system of claim 20, further comprising a control unit, and the control unit is connected to acquire position data from a position measurement device, to one or both: relay the position data to a user and store the position data, and monitor stimulation parameters and results of stimulation simultaneously with the position data.

37. The intravascular electrode system of claim 20, further comprising one or more electrodes for ECG monitoring.

38. An intravascular electrode system comprising: a resiliently-flexible support member;
a plurality of electrodes supported at spaced-apart locations on the resiliently-flexible support member, wherein resilience of the support member is adapted to permit a radius of curvature along a length of an outer surface of the support member to decrease as the support member follows a path of a curved blood vessel, and wherein restoring forces resulting from the resilience of the support member are adapted to hold one or more of the plurality of electrodes in place against a wall of the blood vessel; and
one or more leads within the support member;
wherein the plurality of electrodes are supported on a convex surface of an insulating backing member, the backing member being movable between an expanded configuration and a folded configuration wherein:
when the backing member is in the folded configuration, the electrodes can be retrieved inside a delivery tube; and
when the electrode structure is outside of the delivery tube, the backing member is movable to the expanded configuration.

* * * * *